United States Patent
Pahan

(10) Patent No.: US 12,023,345 B2
(45) Date of Patent: Jul. 2, 2024

(54) COMPOSITIONS AND METHODS FOR TREATING LYSOSOMAL DISORDERS

(71) Applicant: RUSH UNIVERSITY MEDICAL CENTER, Chicago, IL (US)

(72) Inventor: Kalipada Pahan, Skokie, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 91 days.

(21) Appl. No.: 17/036,138

(22) Filed: Sep. 29, 2020

(65) Prior Publication Data

US 2023/0037062 A1 Feb. 2, 2023

Related U.S. Application Data

(62) Division of application No. 15/527,506, filed as application No. PCT/US2015/060878 on Nov. 16, 2015, now abandoned.

(Continued)

(51) Int. Cl.
| | |
|---|---|
| A61K 31/616 | (2006.01) |
| A61K 31/07 | (2006.01) |
| A61K 31/192 | (2006.01) |
| A61K 31/203 | (2006.01) |
| A61K 31/216 | (2006.01) |

(Continued)

(52) U.S. Cl.
CPC ............ *A61K 31/616* (2013.01); *A61K 31/07* (2013.01); *A61K 31/192* (2013.01); *A61K 31/203* (2013.01); *A61K 31/216* (2013.01); *A61K 31/22* (2013.01); *A61K 31/222* (2013.01); *A61K 31/366* (2013.01); *A61K 31/40* (2013.01); *A61K 31/404* (2013.01); *A61K 31/47* (2013.01); *A61K 31/505* (2013.01); *A61K 45/06* (2013.01)

(58) Field of Classification Search
None
See application file for complete search history.

(56) References Cited

U.S. PATENT DOCUMENTS

| | | |
|---|---|---|
| 2001/0028895 A1 | 10/2001 | Bisgaier |
| 2005/0214383 A1 | 9/2005 | Bubnis et al. |

(Continued)

FOREIGN PATENT DOCUMENTS

| | | |
|---|---|---|
| ES | 2 246 737 | 2/2006 |
| WO | 99/38498 A1 | 8/1999 |

(Continued)

OTHER PUBLICATIONS

Lin et al., Biological Psychiatry, vol. 75, Issue 9, May 2014, pp. 678-685 (Year: 2014).*

(Continued)

*Primary Examiner* — Karl J Puttlitz
(74) *Attorney, Agent, or Firm* — Taft Stettinius & Hollister LLP

(57) ABSTRACT

One aspect of the invention provides a method for treatment of a lysosomal storage disorder. The method may include administering to a subject in need of such treatment a composition including a therapeutically effective amount of an agent that mediates upregulation of Transcription Factor EB. In one embodiment, the composition includes a fibrate, such as gemfibrozil or fenofibrate. In another embodiment, the composition also includes all-trans retinoic acid or vitamin A.

8 Claims, 17 Drawing Sheets

Specification includes a Sequence Listing.

Related U.S. Application Data

(60) Provisional application No. 62/081,696, filed on Nov. 19, 2014.

(51) Int. Cl.
| | |
|---|---|
| *A61K 31/22* | (2006.01) |
| *A61K 31/222* | (2006.01) |
| *A61K 31/366* | (2006.01) |
| *A61K 31/40* | (2006.01) |
| *A61K 31/404* | (2006.01) |
| *A61K 31/47* | (2006.01) |
| *A61K 31/505* | (2006.01) |
| *A61K 45/06* | (2006.01) |

(56) References Cited

U.S. PATENT DOCUMENTS

| | | |
|---|---|---|
| 2006/0135612 A1 | 6/2006 | Ferrante |
| 2011/0091442 A1 | 4/2011 | Boyd et al. |
| 2012/0114670 A1 | 5/2012 | Land et al. |
| 2014/0308340 A1 | 10/2014 | Chang et al. |
| 2015/0079161 A1 | 3/2015 | Chang et al. |

FOREIGN PATENT DOCUMENTS

| | | |
|---|---|---|
| WO | 2007/080721 A1 | 7/2007 |
| WO | 2009/040816 A1 | 4/2009 |
| WO | 2010/092112 A1 | 8/2010 |
| WO | 2013/182906 A1 | 12/2013 |
| WO | 2014/089449 A1 | 6/2014 |

OTHER PUBLICATIONS

Carmody et al., N Engl J Med, Nov. 1973, 10-72-1074, Abstract (Year: 1973).*
Loftus et al., Human Molecular Genetics, 2002, vol. 11, No. 24 3107-3114 (Year: 2002).*
Jana et al., J Neuroimmune Pharmacol (2013) 8:739-755 (Year: 2013).*
Ding et al., The Journal of Neuroscience, Nov. 5, 2008, 28(45): 11622-11634 (Year: 2008).*
Database Caplus Chemical Abstracts Service, Columbus, Ohio, US; Database Registry No. 140-10-3, Cinnamic acid, Entered STN: Nov. 16, 1984 (Year: 1984).*
Database Caplus Chemical Abstracts Service, Columbus, Ohio, US; Database Registry No. 532-32-1, Sodium benzoate, Entered STN: Nov. 16, 1984 (Year: 1984).*
Oken R J et al:11 Alzheimer Disease (AD): 1-3, 5, 9 Aspirin Prophylaxis and Therapy 11, Alzheimer Disease, Birkhaeuser, Boston, MA, US, vol. 6, No. 1, Jan. 1, 1992 (Jan. 1, 1992), p. 53/54, XP002062725.
International Search Report for PCT/US2015/060878 dated Feb. 8, 2016, 6 pgs.
Written Opinion for PCT/US2015/060878 dated Feb. 8, 2016, 8 pgs.
Sassano, A et al. Suppressive Effects of Stalins On Acute Promyelocytic Leukemia Cells, Cencer Res. May 1, 2007, vol. 67, No. 9; pp. 4524-4532.
Polito, VA et al. Selective Clearance Of Aberrant Tau Proteins and Rescue Of Neurotoxicity By Transcription Factor EB, EMBO Mol Med. Jul. 28, 2014, vol. 6, No. 9; pp. 1142-1160.
Ghosh, A et al. Activation Of Peroxisome Proliferator-Activated Receptor [alpha] Induces lusosomal Biogenesis In Brain Cells: Implications For Lusosomal Storage Disorders, J Biol Chem. Apr. 17, 2015, vol. 290, No. 16.
Awad. O et al. Altered TFEB-Mediated Lusosomal Biogenesis In Gaucher Disease iPSC-Derived Neuronal Cells, Hu111 Mui Ge11el. Jul. 28, 2015, vol. 24, No. 20; pp. 5775-5788.
Saftig, P., "Physiology of the lysosome", NCBI Bookshelf, National Library of Medicine, 2006, 10 pgs.
Roy, A. et al., "Gemfibrozil, stretching arms beyond lipid lowering", Immunopharmacol Immunotoxicol, vol. 31, No. 3, 2009, pp. 339-351.
Karageorgos, L. E. et al., "Lysosomal Biogenesis in lysosomal Storage Disorders", Exp Cell Res, vol. 234, 1997, pp. 85-97.
Weissmann M.D., G., "The Role of Lysosomes in Inflammation and Disease", Annu Rev Med, vol. 18, 1967, pp. 97-112.
Brignull, L. M. et al., "Reprogramming of lysosomal gene expression by interleukin-4 and Stat6", BMC Genomics, vol. 14, 2013, 20 pgs.
Neufeld, E. F., "Lysosomal Storage Diseases", Annu Rev Biochem, vol. 60, 1991, pp. 257-280.
Gieselmann, V., "Lysosomal storage diseases", Biochim Biophys Acta, vol. 1270, 1995, pp. 103-136.
Khatiwada, B. et al., "Lysosomal storage disease", J Nepal Med Assoc, vol. 48, No. 3, 2009, pp. 242-245.
Jolly, R. D., "Lysosomal Storage Diseases", Neuropathology and Applied Neurobiology, vol. 4, 1978, pp. 419-427.
Appelqvist, H. et al., "The lysosome: from waste bag to potential therapeutic target", J Mol Cell Biol, vol. 5, 2013, pp. 214-226.
Bai, J. et al., "Down-regulated lysosomal processing improved pegylated lipopolyplex—mediated gene transfection", J Gene Med, vol. 15, 2013, pp. 182-192.
Chen, M. H. et al., "Lysosome-Related Genes Are Regulated in the Orbital Fat of Patie with Graves' Ophthalmopathy", Invest Ophthalmol Vis Sci, vol. 49, No. 11, 2008, pp. 4760-4764.
Sarkar, S. et al., "Impaired Autophagy in the Lipid-Storage Disorder Niemann-Pick Type C1 Disease", Cell Rep, vol. 5, 2013, pp. 1302-1315.
Song, W. et al., "2-Hydroxypropyl-B-cyclodextrin Promotes Transcription Factor EB—mediated Activation of Autophagy: Implications for Therapy", J Biol Chem, vol. 289, No. 14, 2014, pp. 10211-10222.
Tsunemi, T. et al., "PGC-1α rescues Huntington's Disease Proteotoxicity by Preventing Oxidative Stress and Promoting TFEB Function", Sci Transl Med, vol. 4, Iss. 142, 2012, 14 pgs.
La Spada, A. R., "PPARGC1A/PGC-1α, TFEB and enhanced proteostasis in Huntington disease: defining regulatory linkages between energy production and protein-organelle quality control", Autophagy, vol. 8, No. 12, 2012, pp. 1845-1847.
Decressac, M. et al., "TFEB-mediated autophagy rescues midbrain dopamine neurons from α-synuclein toxicity", Proc Natl Acad Sci, vol. 110, 2013, pp. E1817-E1826.
Wang, F. et al., "Remodeling the Proteostasis Network to Rescue Glucocerebrosidase Variants by Inhibiting ER-Associated Degradation and Enhancing ER Folding", PLOS One, vol. 8, Iss. No. 4, 2013, 11 pgs.
Song, W. et al., "TFEB regulates lysosomal proteostasis", Hum Mol Genet, vol. 22 No. 10, 2013, pp. 1994-2009.
Medina, D. L. et al., "Transcriptional Activation of Lysosomal Exocytosis Promotes Cellular Clearance", Dev Cell, vol. 21, 2011, pp. 421-430.
Moskot, M. et al., "The Phytoestrogen Genistein Modulates Lysosomal Metabolism and Transcription Factor EB (TFEB) Activation", J Biol Chem, vol. 289, No. 24, 2014, pp. 17054-17069.
Xu, X. et al., "Obesity Activates a Program of Lysosomal-Dependent Lipid Metabolism in Adipose Tissue Macrophages Independently of Classic Activation", Cell Metab, vol. 18, 2013, pp. 816-830.
Singh, R. et al."Lipophagy: Connecting Autophagy and Lipid Metabolism", Int J Cell Biol, 2012, 12 pgs.
Ghosh, A. et al., "Gemfibrozil and Fenofibrate, Food and Drug Administration—approve Lipid-lowering drugs, Up-regulate Tripeptidyl-peptidase 1 in Brain Cells via Peroxisome Proliferator-activated Receptor α: Implications for Late Infantile Batten Disease Therapy", J Biol Chem, vol. 287, No. 46. 2012, pp. 38922-38935.
Xu, J. et al., "Peroxisome proliferator-activated receptor-α agonist fenofibrate regulates IL-12 family cytokine expression in the CNS: relevance to multiple sclerosis", J Neurochem, vol. 103, 2007, pp. 1801-1810.
Xu, J. et al., "Peroxisome proliferator-activated receptor- and retinoid X receptor agonists inhibit inflammatory responses of astrocytes", J Neuroimmunol, vol. 176, 2006, pp. 95-105.

(56) References Cited

OTHER PUBLICATIONS

Krey, G. et al., "Functional Interactions of Peroxisome Proliferator-activated Receptor, Retinoid-X Receptor, and Sp1 in the Transcriptional Regulation of the Acyl—Coenzyme—A Oxidase Promoter", Mol Endocrinol, vol. 9, No. 2, 1995, pp. 219-231.

Juge-Aubry, C. E. et al, "Peroxisome Proliferator-activated Peceptor Mediates Cross-talk with Thyroid Hormone Receptor by Competition for Retinoid X Receptor. Possible Role of a Leucine Zipper-like Heptad Repeat", J Biol Chem, vol. 270, No. 30, 1995, pp. 18117-18122.

Roy, A. et al., "Regulation of Cyclic AMP Response Element Binding and Hippocampal Plasticity-Related Genes by Peroxisome Proliferator-Activated Receptor α", Cell Rep, vol. 4, 2013, pp. 724-737.

Marcus, S. L. et al., "Transactivation by PPAR/RXR Heterodimers in Yeast is Potentiated by Exogenous Fatty Acid Via a Pathway Requiring Intact Peroxisomes", Gene Expr, vol. 4, 1995, pp. 227-239.

Parast, M. M. et al., "PPARγ. Regulates Trophoblast Proliferation and Promotes Labyrinthine Trilineage Differentiation", PLoS One, vol. 4, Iss Nol. 11, 2009, 13 pgs.

Leung, F. W., "Risk factors for Gastrointestinal Complications in Aspirin Users: Review of Clinical and Experimental Data", Dig Dis Sci, vol. 53, 2008, pp. 2604-2615.

Budd, J. S. et al., "The effectiveness of low dose slow release aspirin as an antiplatelet agent", J R Soc Med, vol. 86, 1993, pp. 261-263.

Laudanno, O. M., "Cytoprotective Effect of S-Adenosylmethionine Compared with That of Misoprostol against Ethanol-, Aspirin-, and Stress-Induced Gastric Damage", Am J Med, vol. 83, 1987, pp. 43-47.

"Modulation of Micro-RNA Pathways by Gemfibrozil in Predementia Alzheimer" at https://clinicaltrials.gov/ct2/show/NCT02045056 (Year: 2014).

Geroldi, D. et al.; "Stimulation of proteasome by all-trans-retinoic acid: A novel therapeutic approach for lysosomal storage diseases?"; Medical Hypotheses, vol. 69, No. 4; Nov. 13, 2006; p. 913.

Rao et al., "Cinnamon: A Multifaceted Medicinal Plant," Evidence-Based Complementary and Alternative Medicine, Apr. 10, 2014, 12 pgs.

De Duve, C. "Lysosomes, a New Group of Cytoplasmic Particles", Subcellular particles, a Symposium at Society of General Physiologists at Woods Hole, MA, 1959, vol. 60, pp. 128-159.

De Duve, Christian et al., "Functions of Lysosomes", The Rockefeller University, Annu. Rev. Physiol., 1966 vol. 28, pp. 435-492.

Perez-Sala, Dolores et al., "The C-Terminal Sequence of RhoB Directs Protein Degradation through an Endo-Lysosomol Pathway", PLoS One, Dec. 2009, vol. 4, Issue 14, pp. 1-14.

Fuster, Jose J. et al., "Tumor suppressor p27kip1 undergoes endolysosomal degradation through its interaction with sorting nexin 6", Mar. 2010, The FASEB Journal, vol. 24, No. 8, pp. 2998-3009.

Korolchuk, Viktor I. et al., "Lysosomal positioning coordinates cellular nutrient responses", Nat. Cell Biol., 2011, vol. 13, No. 4, pp. 453-460.

Boya, P. et al., "Lysosomal membrane permeabilization in cell death", Oncogene, 2008, vol. 27, pp. 6434-6451.

Martina, Jose A. et al., "The Nutrient-Responsive Transcription Factor TFE3 Promotes Autophagy, Lysosomal Biogenesis, and Clearance of Cellular Debris", Science Signaling, 2014, vol. 7, Issue 309, pp. 1-16.

Palmieri, Michela et al., "Characterization of the CLEAR network reveals an integrated control of cellular clearance pathways", Human Molecular Genetics, 2011 vol. 20, No. 19 pp. 3852-3866.

Sardiello, Marco et al., "A Gene Network Regukating Lysosomal Biogenesis and Function", Science, 2009, vol. 325, pp. 473-477.

Marschner, Katrin et al., "A Key Enzyme in the Biogenesis of Lysosomes Is a Protease That Regulates Cholesterol Metabolism", Science, 2011, vol. 333, pp. 87-90.

Settembre, Carmine, et al., "TFEB Links Autophagy to Lysosomal Biogenesis", Science, 2011, vol. 332, pp. 1429-1433.

Ferron, Mathieu et al., "A RANKL-PKCβ-TFEB signaling cascade is necessary for lysosomal biogenesis in osteoclasts", Genes & Development, 2013, vol. 27, pp. 955-969.

Settembre, Carmine et al., "A lysosomal-to-nucleus signaling mechanism senses and regulates the lysosome via mTOR and TFEB", The EMBO Journal, 2012, vol. 31, No. 5, pp. 1095-1108.

Settembre, Carmine et al., "Signals for the lysosome: a control center for cellular clearance and energy metabolism", Nat Rev Mol Cell Biol., 2013, vol. 14, No. 5, pp. 283-296.

Settembre, Carmine et al., "TFEB controls cellular lipid metabolism through a starvation-induced autoregulatory loop", Nat Cell Biol., 2013, vol. 15, No. 6, pp. 647-658.

Robins, Sander, et al., "Relation of Genfibrozil Treatment and Lipid Levels With Major Coronary Events", JAMA, 2001, vol. 285, No. 12, pp. 1585-1591.

Rubins H.B. et al., "Effect of reduction of plasma triglycerides with gemfibrozil on high-density-lipoprotein-cholesterol concentrations", Journal of Internal Medicine, 1992, vol. 231, pp. 421-426.

Rubins, Hanna Bloomfield et al., "Gemfibrozil for the Secondary Prevention of Coronay Heart Disease in Men With Low Levels of High-Density Lipoprotein Cholesterol", The New York Journal of Medicine, 1999, vol. 341, No. 6, pp. 410-418.

Dasgupta, Subhajit et al., "Gemfibrozil Ameliorates Relapsing-Remitting Experimental Autoimmune Encephalomyelitis Independent of Peroxisome Proliferator-Activated Receptor-α", Mol Pharmacology, 2007, vol. 72, No. 4, pp. 934-946.

Pahan, Kalipada et al., "Gemfibrozil, a Lipid-lowering drug, Inhibits the Induction of Nitric-oxide Synthase in Human Astrocytes", J Biol. Chem., 2002, vol. 277, No. 48, pp. 45984-45991.

Corbett, Grant T. et al., "Gemfibrozil, a lipid-lowering drug, upregulates interleukin-1 receptor antagonist in mouse cortical neurons: implications for neuronal self-defense", J. Immunol., 2012, vol. 189, No. 2, pp. 1002-1013.

Brahmachari, Saurav et al., "Sodium Benzonate, a Food Additive and a Metabolite of Cinnamon, Modifies T Cells at Multiple Steps and Inhibits Adoptive Transfer of Experimental Allergic Encephalomyelitis", J. Immunol., 2007, vol. 169, No. 1, pp. 275-283.

Saha, Ramendra N. et al., "Differential regulation of Mn-superoxide dismutase in neurons and astroglia by HIV-1 gp120: Implications for HIV-associated dementia", Free Radic Biol. Med., 2007, vol. 43, No. 12, pp. 1966-1878.

Giulian, dana et al., "Characterization of Ameboid Microglia Isolated from developing Mammalian Brain", The Journal of Neuroscience, 1986, vol. 6, No. 8, pp. 2163-2178.

Jana, Malabendu et al., "Redox regulation of cytokine-mediated inhibition of myelin gene expression in human primary oligodendrocytes", Free Radic Biol. Med., 2005, vol. 39, No. 6, pp. 832-831.

Khasnavis, Saurabh et al., "Suppression of Nuclear Factor-←B Activation and Inflammation in Microglia by Physically Modified Saline", The Journal of Biological Chemistry, 2012, vol. 287, No. 35, pp. 29529-29542.

Khasnavis, Saurabh et al., "Sodium Benzonate, a Metabolite of Cinnamon and a Food Additive, Upgrades Neuroprotective Parkinson Disease Protein DJ-1 in Astrocytes and Neurons", J. Neuroimmune Phar,acol., 2012, vol. 7, No. 2, pp. 424-435.

Dasgupta, Subhajit et al., "Antineuroinflammatory Effect of NF-κB Essential Modifier-Binding Domain Peptides in the Adoptive Transfer Model of Experimental Allergic Encephalomyelitis", J. Immunol., 2004, vol. 173, pp. 1344-1354.

Corbett, Grant T. et al., "Gemfibrozil, a lipid-lowering draug, upregulates interleukin-1 receptor antagonist in mouse cortical neurons: Implications for neuron self-defense", J. Immunol., 2012, vol. 189, No. 2, pp. 1002-1013.

Saha, Ramendra N. et al., "Up-regulation of BDNF in Astrocytes by TNF-α: A Case for the Neuroprotective Role of Cytokine", J Neuroimmune Pharmacol., 2006, vol. 1, No. 3, pp. 212-222.

Jana, Malabendu et al., "Involvement of Phosphatidylinositol 3-Kinase-Mediated Up-regulation of I kBα in Anti-Inflammatory Effect of Gemfibrozil in Microglia", J. Immunol., 2007, vol. 1793, pp. 4142-4152.

(56) References Cited

OTHER PUBLICATIONS

Jana, Malabendu et al., "Gemfibrozil, a lipid lowering drug, inhibits and activation of primary human microglia via peroxisome proliferator-activated receptor β", Nerocchem Res., 2012, vol. 37, No. 8, pp. 1718-1729.

Nelson, Joel D. et al., "Protocol for the fast chromatin immunoprecipitation *ChIP) method", Nature Protocols, 2006, vol. 1, No. 1, pp. 179-185.

Cullingford, Tim E., et al., "Distribution of mRNAs Encoding the Peroxisome Proliferator-Activated Receptor α, β and y and the Retinoid X Receptor α, β and y in Rat Central Nervous System", J Neorochem., 1998, vol. 70, No. 4, pp. 1366-1375.

Nishizawa, Hanako et al., "Effects of In Utero Exposure to Bisphenol A on Expression of RARα and RXRα mRNAs in Murine Embryos", J. Reprod. Dev., 2003, vol. 49, pp. 539-545.

Chinetti, Giulia et al., "Activation of Proliferator-activated receptors α and y Induces Apoptosis of Human Monocyte-derived Macrophages", J. Biol. Chem., 1998, vol. 273, No. 40, pp. 25573-25580.

Brun, Sonia et al., "A Potential of Peroxisome Proliferator-Activated Receptor-α Induce the Expression of the Uncoupling Protein-3 Gene in Skeletal Muscle", Diabetes, 1999, vol. 48, pp. 1217-1222.

Chinetti, Giulia et al., "PPAR-α and PPAR-y activators induce cholesterol removal from human macrophage foam cells through stimulation of the ABCA1 pathway", Nature Medicine, 2001, vol. 7 No. 1, pp. 53-58.

Kelly, Daniel P., "The Pleiotropic Nature of the Vascular PPAR Gene Regulatory Pathway", Circ Res., 2001, vol. 89, pp. 935-937.

Boitier, Eric et al., "Advances in understanding the regulation of apoptosis and mitosis by peroxisome-proliferator activated receptors in pre-clinical models: relevance for human health and disease", Comparative Hepatology, 2003, vol. 2, No. 3, pp. 1-15.

Pshezhetsky, Alexey et al., "Lysosomal Multienzyme Complex: Biochemistry, Genetics, and Molecular Pathophysiology", Progress in Nucleic Acid Research and Molecular Biology, 2001, vol. 69, pp. 81-114.

Eskelinen, Eeva-Liisa et al., "At the acidic edge: emerging functions for lysosomal membrane proteins", Cell Biology, 2003, vol. 13, No. 3, pp. 137-145.

Extended European Search Report for EP 15861122 issued Mar. 28, 2018, 12 pgrs.

Hanna Appelqvist et al: 11 The lysosome: from waste bag to potential therapeutic target 11, Journal of Molecular Cell Biology, vol. 5, No. 4, Aug. 1, 2013 (Aug. 1, 2013), pp. 214-226, XP055460132, ISSN: 1674-2788, DOI: 10.1093/jmcb/mjt022 11 Lysosomes in diseases 11; p. 220.

Wensi Song et al: 11 2-Hydrixypropyl-?-cycodextrin Promotes Transcription Factor EB-mediated Activation of Autophagy: Implications for Therapy 11 Journal of Biological Chemistry, vol. 289, No. 14, Apr. 4, 2014 (Apr. 4, 2014), pp. 10211-10222, XP055386213, us ISSN: 0021-9258, DOI: 10.1074/jbc.M113.506246 pp. 10212, left hand column, last paragraph—right-hand column, paragraph 1.

A. Ghosh et al: 11 Gemfibrozil and 1-3, 6-1: Fenofibrate, Food and Drug Administration-approved Lipid-lowering Drugs, Up-regulate Tripeptidyl-peptidase 1 in Brain Cells via Peroxisome Proliferator-activated Receptor?: Implications for Late Infantile Batten Disease Therapy 11, Journal of Biological Chemistry, vol. 287, No. 46, Sep. 18, 2012 (Sep. 18, 2012), pp. 38922-38935, XP55099483, ISSN: 0021-9258, DOI: 10.1074/jbc.M112.365148.

* cited by examiner

Figure 9(A)-(D)

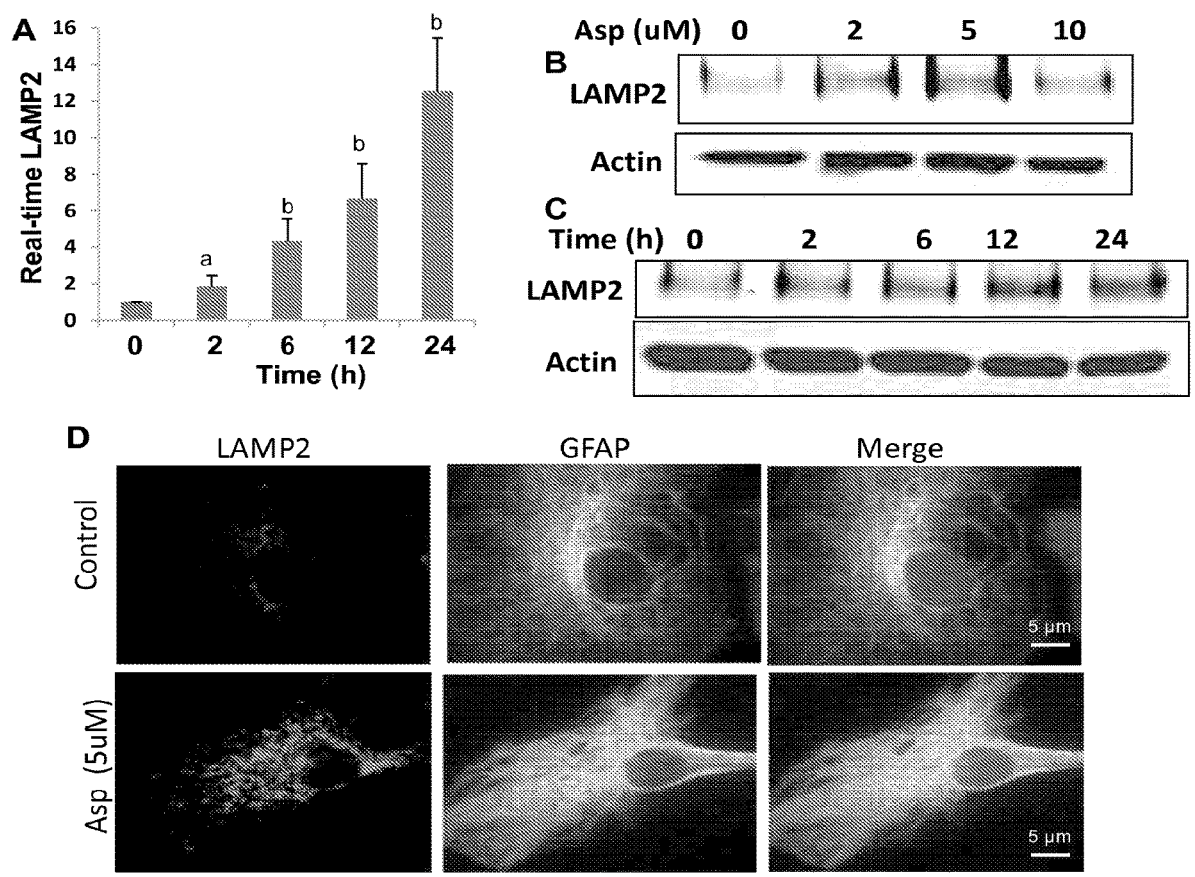
Figure 11(A)-(D)

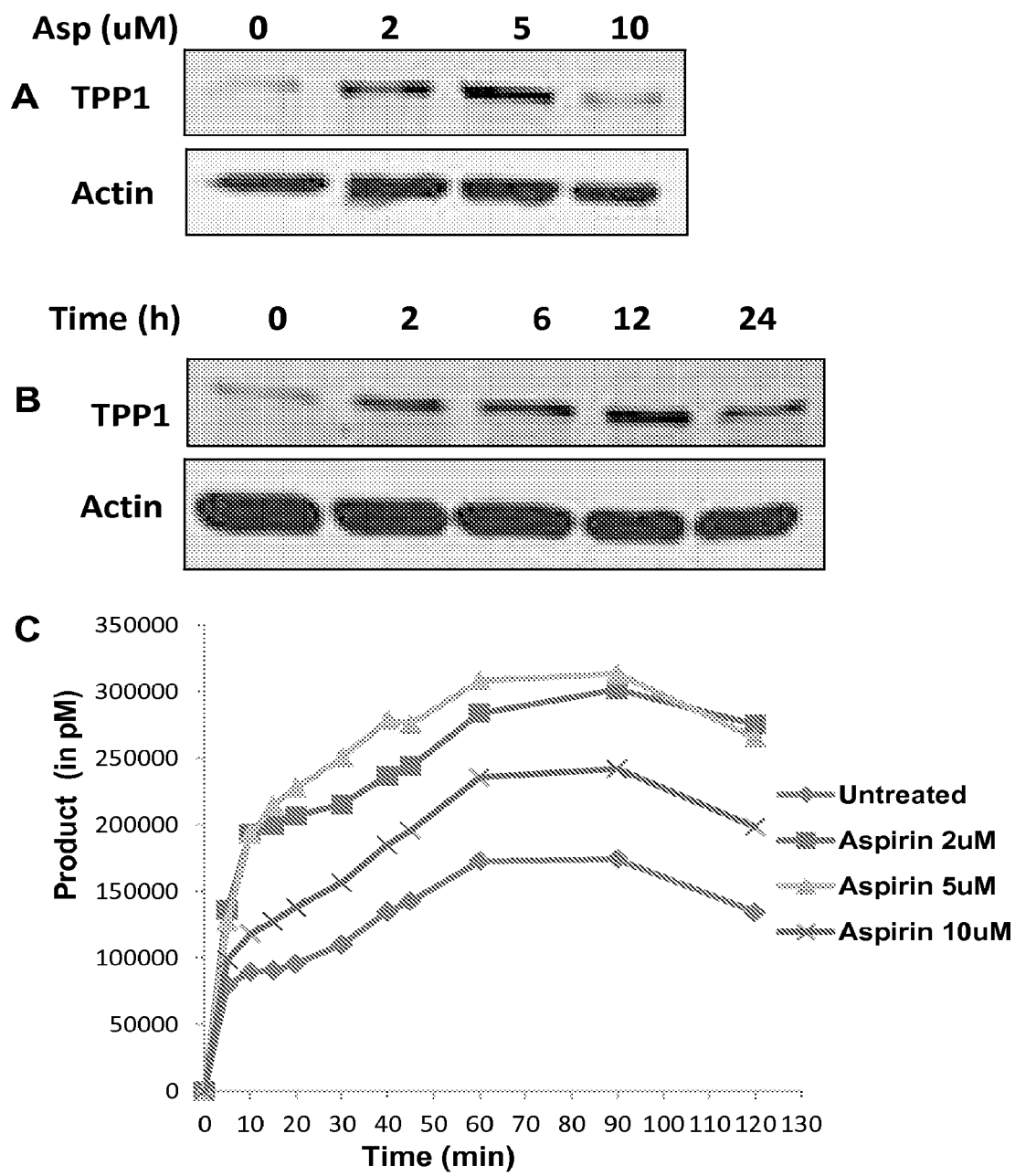
Figure 12 (A)-(C)

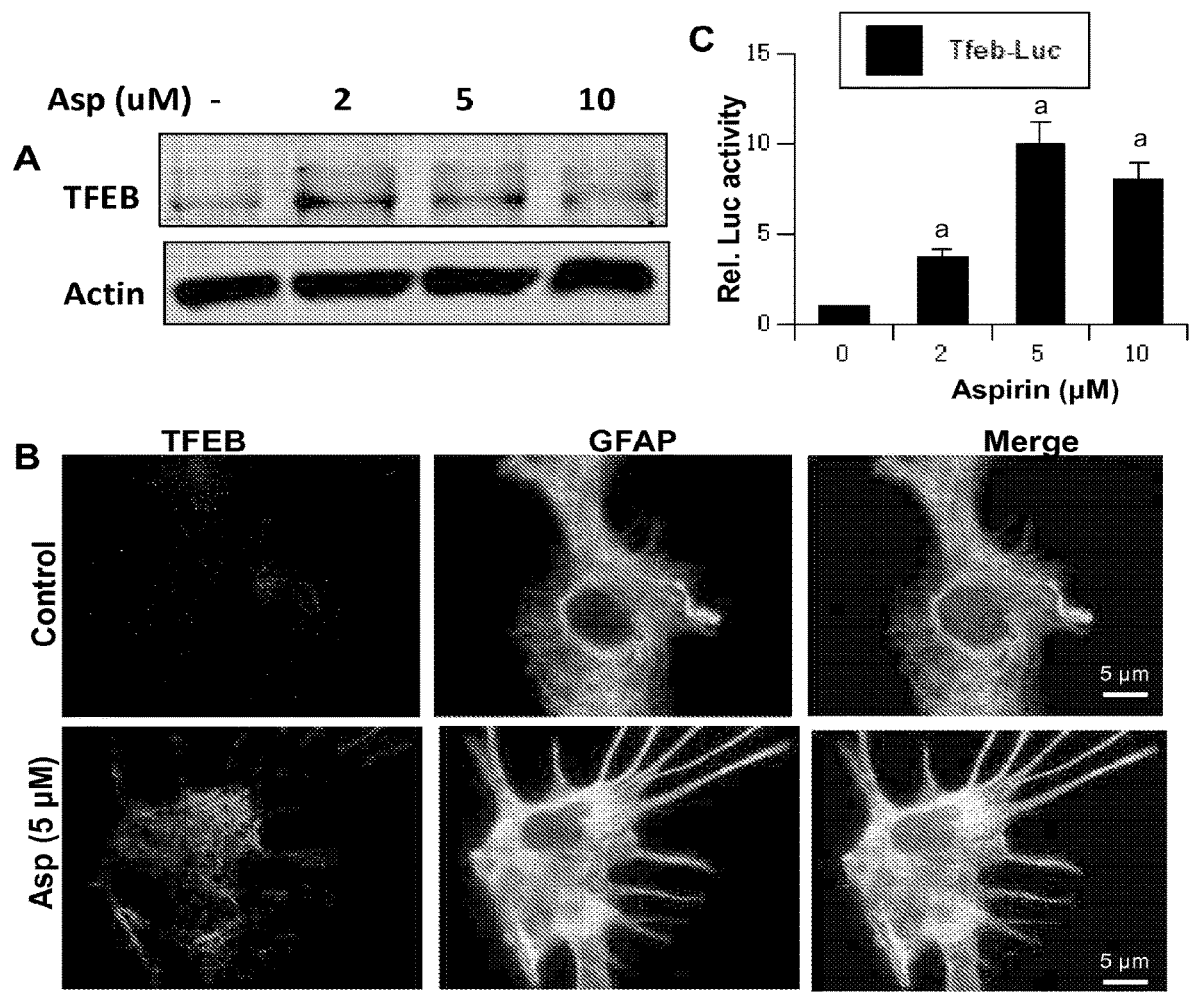
Figure 13(A)-(C)

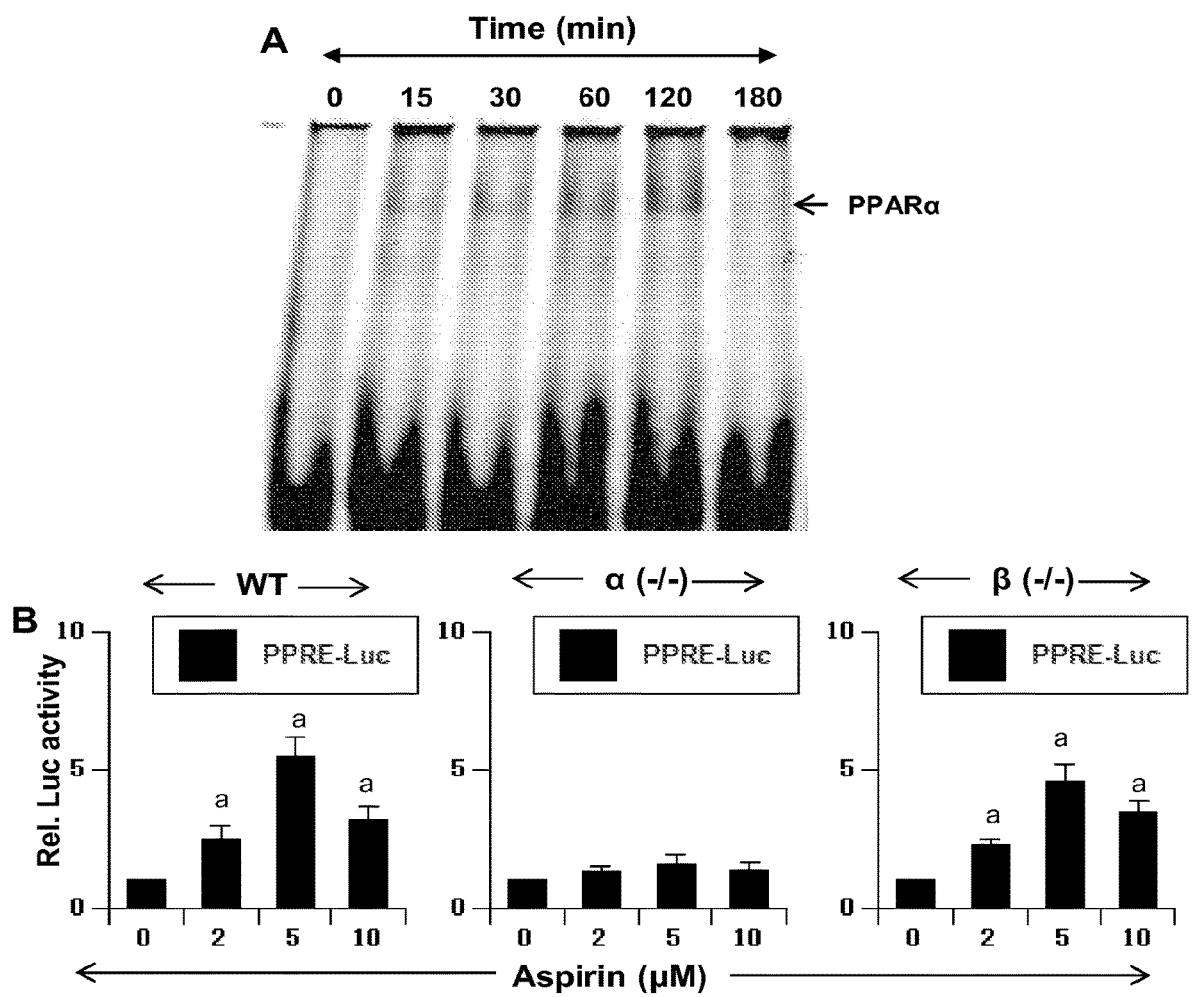
Figure 14(A)-(B)

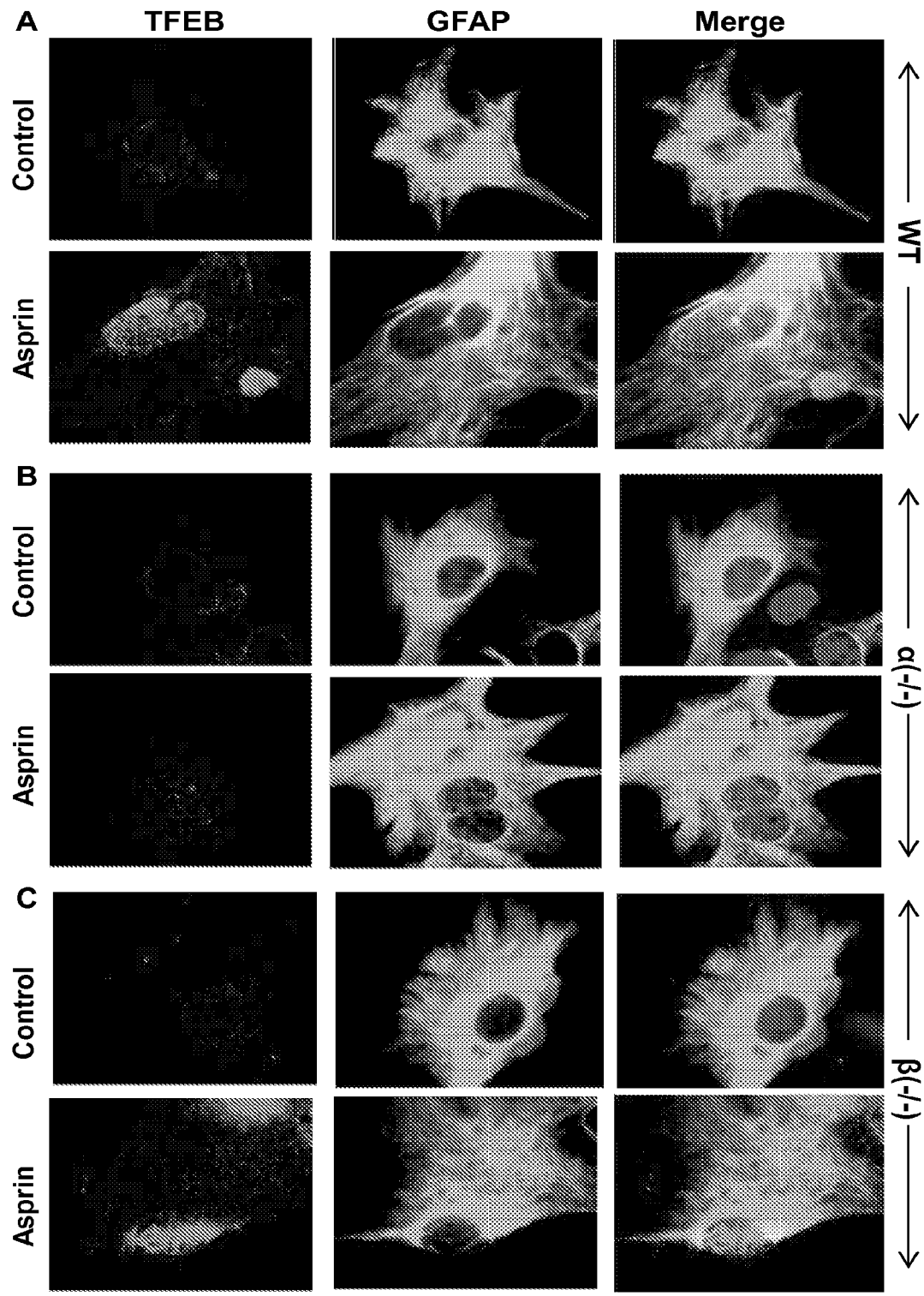
Figure 15(A)-(C)

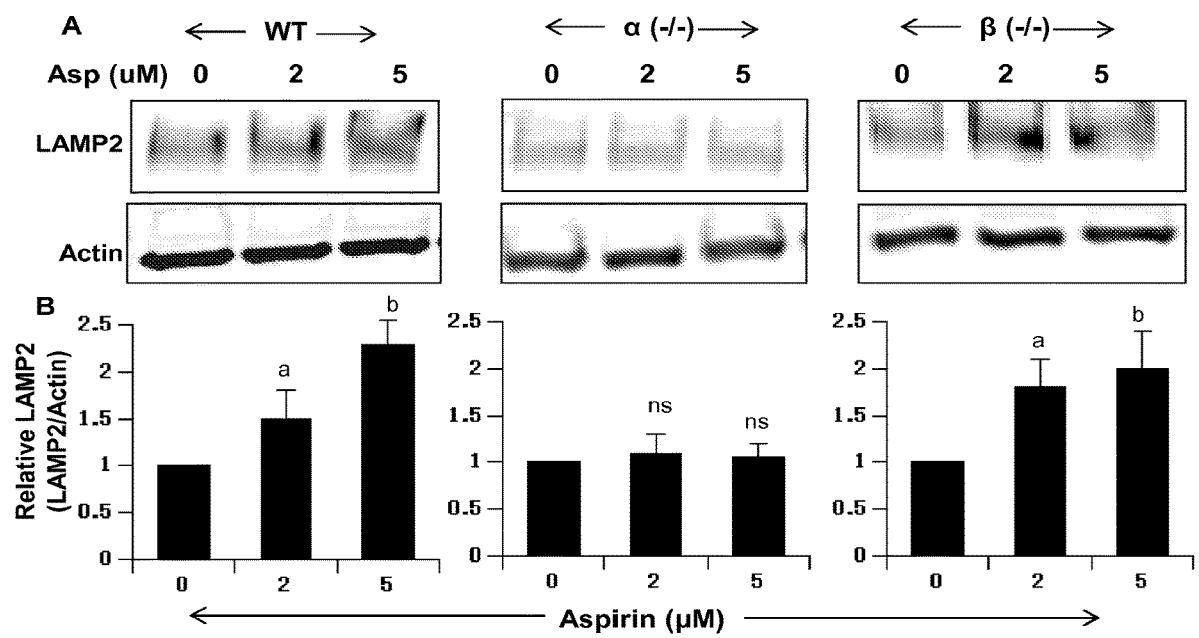
Figure 16(A)-(B)

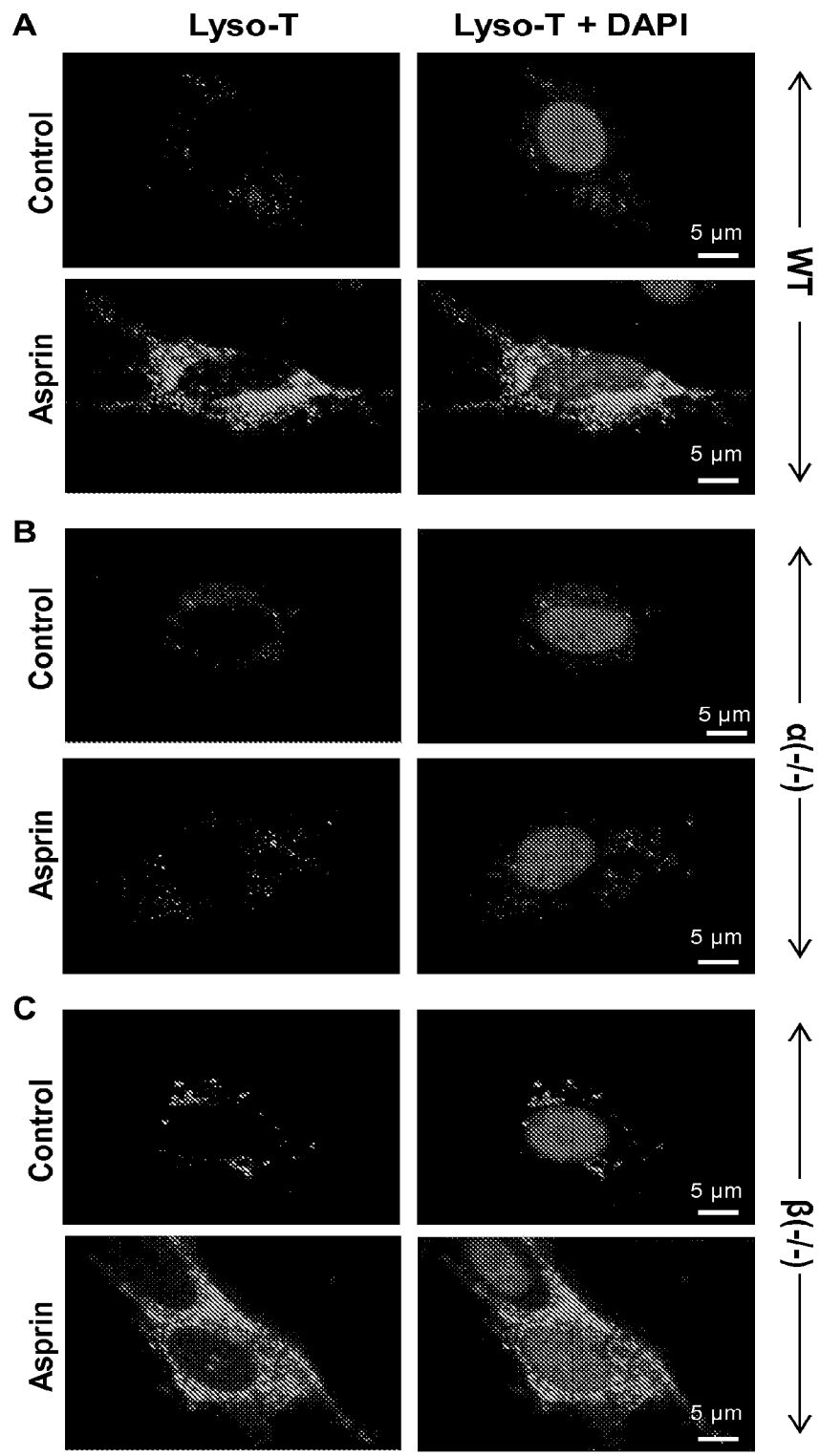
Figure 17(A)-(C)

COMPOSITIONS AND METHODS FOR TREATING LYSOSOMAL DISORDERS

RELATED APPLICATIONS

This application is a divisional of U.S. patent application Ser. No. 15/527,506, which is a National Stage of PCT/US2015/060878, filed Nov. 16, 2015, which, claims the benefit of the filing date of U.S. Provisional Patent Application No. 62/081,696, filed Nov. 19, 2014, the contents of which applications are hereby incorporated by reference.

TECHNICAL FIELD

The present invention generally relates to compositions and methods for treating lysosomal storage disorders.

BACKGROUND

Lysosomes are membrane bound organelles containing a host of hydrolytic enzymes that are highly active in acidic milieu (1-3). Classically identified as the waste management organelle, lysosomes have been shown to be involved in major cellular processes including degradation developmental, programmed cell death, and nutritional responses (2, 4-8). The diverse roles and responses of the lysosome to different stimuli suggest a coordinated regulation of expression of lysosomal genes (9, 10). Recent studies provide modest information about the regulation of lysosomal genes (11, 12) but pattern discovery analysis for the lysosomal genes revealed the presence of a Coordinated Lysosomal Expression and Regulation (CLEAR) element, which is a potential binding site for Transcription Factor EB (TFEB), a member of the microphthalmia-transcription factor E (MiT/TFE) subfamily of bHLH (basic helix-loop-helix) factors. The study reports a potential link between TFEB and lysosomal biogenesis (9, 10, 12).

The regulation of Tfeb appears to be complex and dependent on cell type and stimuli. In differentiated osteoclasts, a RANKL-dependent signaling pathway induces TFEB activation induced lysosomal biogenesis (13). Starvation or stress conditions may also activate TFEB, which otherwise is maintained in an inactivated state by mTORC1 (14, 15). One study also showed starvation induced TFEB activity can play a vital role in lipid metabolism and that activated TFEB can also autoregulate its own gene expression (16).

Lysosomal storage diseases (LSDs) are a group of approximately 50 rare inherited metabolic disorders that result from defects in lysosomal function. The symptoms of LSD vary, depending on the particular disorder and other variables like the age of onset, and can be mild to severe. They can include developmental delay, movement disorders, seizures, dementia, deafness and/or blindness. Some people with LSD have enlarged livers (hepatomegaly) and enlarged spleens (splenomegaly), pulmonary and cardiac problems, and bones that grow abnormally.

SUMMARY OF THE PREFERRED EMBODIMENTS

One aspect of the present invention provides a method for treatment of a LSD. The method may include administering to a subject in need of such treatment a composition including a therapeutically effective amount of an agent that mediates upregulation of Transcription Factor EB (TFEB).

In one embodiment, the agent is a statin. For example, the statin may be atorvastatin, fluvastatin, lovastatin, pitavastatin, pravastatin, rosuvastatin, or simvastatin. The agent may also be, for example, a lipid-lowering drug, such as a fibrate. In some embodiments, the fibrate is gemfibrozil or fenofibrate. In other embodiments, the agent is an analgesic, an antipyretic, aspirin, a cinnamon metabolite, cinnamic acid, sodium phenylbutyrate or sodium benzoate. In yet other embodiments, the composition may include a combination of at least two of the above agents.

The composition may also include all-trans retinoic acid or vitamin A. For example, the composition may include a statin or a fibrate and all-trans retinoic acid or vitamin A. This combination of the agent(s) with all-trans retinoic acid or vitamin A may provide a greater therapeutic effect in the subject than administration of the all-trans retinoic acid, vitamin A or the fibrate alone. The combination may be a synergistic combination. TFEB may also be upregulated by increasing Transcription Factor EB mRNA levels increasing Transcription Factor EB protein levels or activating a PPARa-RXRa heterodimer.

The LSD may be a neurodegenerative disorder, for example, neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) or dementia with Lewy bodies (DLB). In another embodiment, the LSD is a disorder of the autophagy pathway and wherein the agent increases lysosomal biogensis.

In other embodiments, the LSD is Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, Galactosialidosis, or Batten disease including late infantile Batten disease and Juvenile Batten disease.

Another aspect of the present invention provides a method for treatment of a LSD including administering to a subject in need of such treatment a composition including a therapeutically effective amount of an agent that mediates upregulation of the Tfeb gene. Yet another aspect provides a method for treatment of a LSD including administering to a subject in need of such treatment a composition including a therapeutically effective amount of an agent, wherein the agent restores TFEB activity.

BRIEF DESCRIPTION OF THE DRAWINGS

FIG. 11(A)-(D) shows the upregulation of LAMP2 expression by aspirin in primary mouse astrocytes. 11(A) Cells were treated with 5 μM aspirin for different time periods under serum-free condition followed by monitoring the mRNA expression of LAMP2 by real-time PCR. Results are mean +SD of three different experiments. ap<0.05 vs control; bp<0.001 vs control. 11(B) Cells were treated with different concentrations of aspirin for 24 h under serum-free condition followed by Western blot for LAMP2. 11(C) Cells were treated with 5 μM aspirin for different time periods under serum-free condition followed by Western blot for LAMP2. 11(D) After 24 h of aspirin treatment, cells were double-labeled for LAMP2 and GFAP. Results represent three independent experiments.

FIG. 12(A)-(C) shows an increase in TPP1 by aspirin in primary mouse astrocytes. 12(A) Cells were treated with different concentrations of aspirin for 24 h under serum-free condition followed by Western blot for TPP1. 12(B) Cells were treated with 5 μM aspirin for different time periods under serum-free condition followed by Western blot for TPP1. Actin was run as a house keeping molecule. 12(C) Cells were treated with different concentrations of aspirin for 24 h under serum-free condition followed by TPP1 activity assay using cell extract containing 5 μg of total protein and Ala-Ala-Phe 7-amido-4-methylcoumarin as substrate. Results represent three independent experiments.

FIG. 13(A)-(C) illustrates the upregulation of TFEB by aspirin in primary mouse astrocytes. 13(A) Cells were treated with different concentrations of aspirin for 12 h under serum-free condition followed by Western blot for TFEB. Actin was run as a house keeping molecule. 13(B) Cells were treated with 5 μM aspirin for 12 h under serum-free condition followed by double-labeling with GFAP and TFEB. These results are mean of two independent experiments. 13(C) Cells were transfected with p(WT)Tfeb-Luc plasmid and after 24 h of transfection, cells were stimulated with different doses of aspirin. After 4 h, firefly luciferase activity was measured in total cell extracts. Results are mean +SD of three different experiments. $^a$p<0.001 vs control.

FIG. 14(A)-(B) illustrates activation of PPARα by aspirin in primary mouse astrocytes. 14(A) Cells were treated with 5 μM aspirin for different min intervals followed by isolation of nuclear extracts and electrophoretic mobility shift assay for monitoring DNA-binding activity of PPARα using PPARα-binding site of the Tfeb promoter as a probe. 14(B) Astrocytes isolated from wild type, PPARα (−/−) and PPARβ (−/−) mice were transfected with PPAR luciferase reporter (PPRE-x3-TK-luc) plasmid and after 24 h of transfection, cells were stimulated with different doses of aspirin. After 4 h, firefly luciferase activity was measured in total cell extracts. Results are mean +SD of three different experiments. $^a$p<0.001 vs control.

FIG. 15(A)-(C) illustrates that aspirin increases the level of TFEB in astrocytes via PPARα. Astrocytes isolated from WT 15(A), PPARα (−/−) 15(B) and PPARβ (−/−) 15(C) mice were treated with 5 μM aspirin for 12 h under serum-free condition followed by double-labeling for TFEB and GFAP. Results represent three independent experiments.

FIG. 16(A)-(B) illustrates that aspirin increases the level of LAMP2 in astrocytes via PPARα. Astrocytes isolated from WT, PPARα (−/−) and PPARβ (−/−) mice were treated with different concentrations of aspirin for 24 h under serum-free condition followed by Western blot analysis for LAMP2 16(A). Actin was run as a house keeping molecule. Bands were scanned and expressed as relative to control 16(B). Results are mean +SD of three different experiments. $^a$p<0.05 vs control; $^b$p<0.001 vs control. ns, not significant.

FIG. 17 (A)-(C) illustrate that aspirin increases lysosomal biogenesis in astrocytes via PPARα. Astrocytes isolated from WT 17(A), PPARα (−/−) 17(B) and PPARβ (−/−) 17(C) mice were treated with 5 µM aspirin for 24 h under serum-free condition followed by Lyso-tracker staining. Results represent three independent experiments.

DETAILED DESCRIPTION OF THE PREFERRED EMBODIMENTS

Definitions

Figure 1:
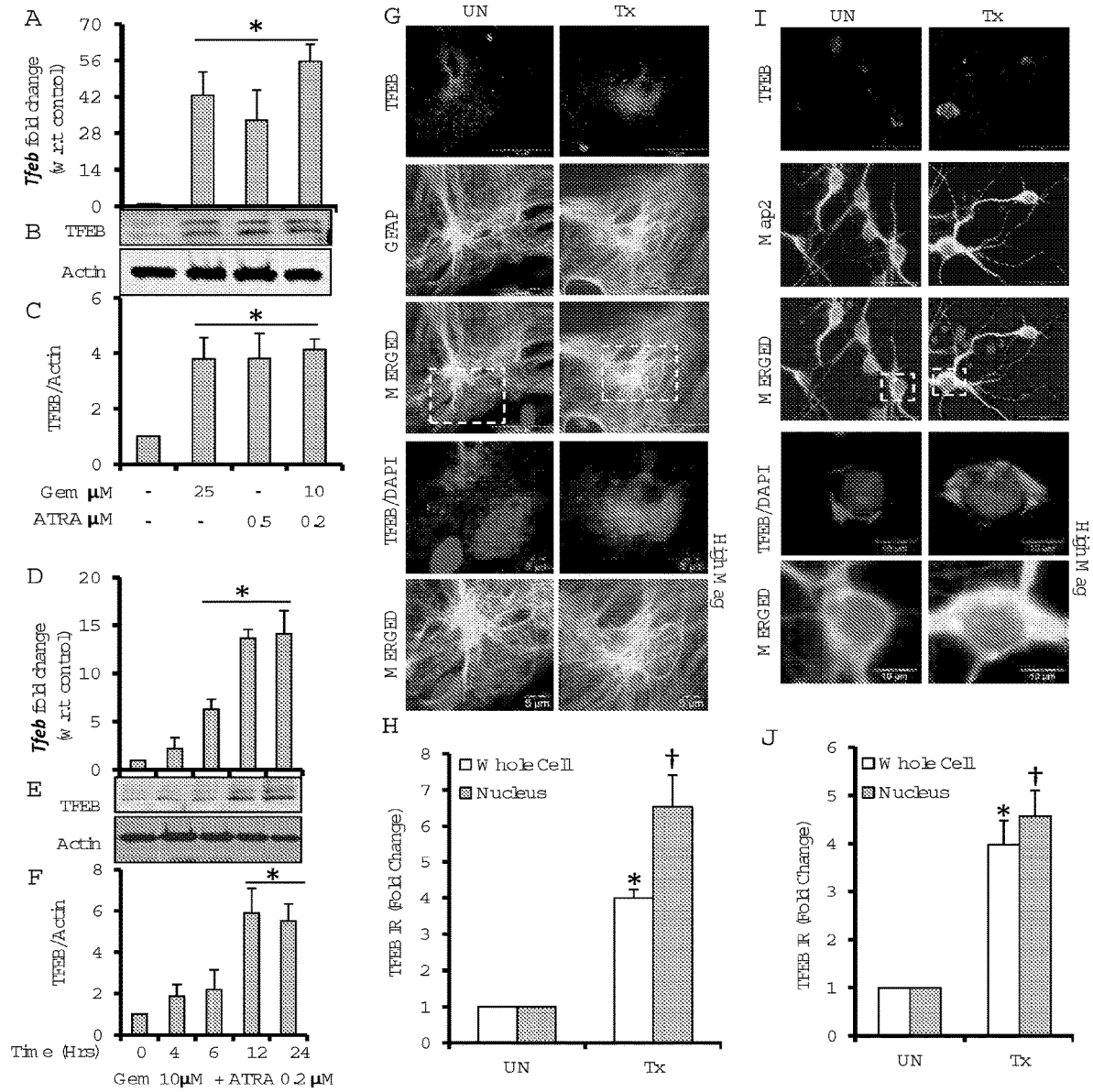
FIG. 1 shows Gemfibrozil and Retinoic Acid upregulating TFEB mRNA and protein levels in brain cells. (A, B) Mouse primary astrocytes were treated with different concentrations of gemfibrozil and all-trans retinoic acid (ATRA) under serum free DMEM/F-12 medium for 12 hrs followed by monitoring mRNA levels of Tfeb by qRT-PCR (A) and TFEB protein levels by immunoblot (B). (C) Densitometric analysis of the immunoblot for TFEB (relative to β-Actin). (D, E), Mouse primary astrocytes were treated with a combination of gemfibrozil (10 μM) and ATRA (0.2 μM) for 4, 6, 12 and 24 hrs under similar culture conditions followed by monitoring of mRNA levels of TFEB by qRT-PCR (D) and protein levels by immunoblot (E). (F), denistometric analysis for the immunoblot for TFEB. All results are representative of or mean ±SEM of at least three independent set of experiments. (G, I) Mouse primary astrocytes (G) and mouse primary neurons (I) were treated with combination of gemfibrozil and retinoic acid under serum free condition for 24 hrs and were double labeled for TFEB (red)—GFAP (green) and TFEB (red)—Map2 (green), respectively. DAPI was used to stain nuclei. Scale bar=20 μM (for G), scale bar=5 μM for High Magnification Images (for G); Scale bar=50 μM (for I), scale bar=10 μM for High Magnification Images (for I). (H,J) Quantification of TFEB immunoreactivity (TFEB IR) in whole cell and nucleus for mouse primary astrocytes (H) and mouse primary neurons (J) calculated as fold over control. At least 25 separate images per condition from three independent set of experiments are quantified using ImageJ. p†<0.05 vs untreated control.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

As used herein, the term subject refers to a human or veterinary subject. The term "therapeutic effect" as used herein means an effect which induces, ameliorates or otherwise causes an improvement in the pathological symptoms, disease progression or physiological conditions associated with or resistance to succumbing to a disorder, for example a LSD, of a subject. The term "therapeutically effective amount" as used with respect to a drug means an amount of the drug which imparts a therapeutic effect to the subject.

The terms "synergy", "synergism" or "synergistic" mean more than the expected additive effect of a combination. A synergistic effect may be attained when the active ingredients are: (1) co-formulated and administered or delivered simultaneously in a combined, unit dosage formulation; (2) delivered by alternation or in parallel as separate formulations; or (3) by some other regimen.

Compositions and Methods for Treating Lysosomal Storage Disorders

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One aspect of the present invention relates to methods of treatment of a lysosomal storage disorder (LSD). The LSD may be, for example, Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, Galactosialidosis or Batten disease including late infantile Batten disease and Juvenile Batten disease. The LSD may also be a neurodegenerative disease involving the autophagy-lysosome pathway, for example, neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) or dementia with Lewy bodies (DLB). The neurodegenerative disorder may be characterized by defective autophage. Such disorders include Alzheimer's, Parkinson's disease, and Huntington's disease.

One embodiment includes administering to a subject suffering from a LSD an agent that upregulates or enhances expression from the Tfeb gene. Upregulation may include increasing mRNA levels for Tfeb. The methods of the present invention also include administering to a subject suffering from a LSD an agent that upregulates TFEB or restores TFEB activity. Upregulation may include increasing TFEB mRNA levels, increasing TFEB protein levels, or increasing TFEB activity. Activating a PPARα/RXRα heterodimer results in upregulation of TFEB. The inventor has also surprisingly shown that TFEB is upregulated through the activity or involvement of PPARα, but not PPARβ or PPARγ.

The agent may be a lipid-lowering drug such as a fibrate. The fibrate may be gemfibrozil, fenofibrate, or clofibrate. The agent may be all-trans retinoic acid or vitamin A. Surprisingly and unexpectedly, administration of the fibrate in combination with all-trans retinoic acid or vitamin A to the subject may upregulate TFEB more than administration of the fibrate or all-trans retinoic acid or vitamin A alone. The fibrate and all-trans retinoic acid or vitamin A, when administered together to the subject, may cooperatively enhance upregulation of TFEB to synergistically upregulate TFEB. A lower dose of the fibrate may be needed in the presence of all-trans retinoic acid or vitamin A to achieve the same degree of TFEB upregulation as occurs when only a higher dose of the fibrate is administered to the subject. The combination of the fibrate and all-trans retinoic acid or vitamin A may be a synergistic combination.

In other embodiments, the lipid lowering drug is a statin. For example the statin may be atorvastatin, fluvastatin, lovastatin, pitavastatin, pravastatin, rosuvastatin, simvastatin or a combination of at least two of these drugs. The statin or statins may be used alone or in combination with a fibrate and or all-trans retinoic acid or vitamin A. In yet other embodiments, the agent may be an analgesic or antipyretic, for example aspirin; phenylbutyrate; sodium benzoate; or a cinnamon metabolite, for example cinnamic acid. Again, such agents may be used in combination with all-trans retinoic acid or vitamin A and may be administered together to the subject to cooperatively enhance upregulation of TFEB to synergistically upregulate TFEB.

The lipid lowering drugs may be drugs that reduce the level of triglycerides circulating in the blood of the subject. Additionally, lipid-lowering drugs may be drugs that decrease the risk of hyperlipidemia. The fibrate may mediate upregulation of TFEB via PPARα, but not PPARβ and PPARγ. During upregulation of TFEB, PPARα forms a heterodimer with RXR-α and the RXRα/PPAR-α heterodimer is recruited to the promoter of the Tfeb gene via a RXR binding site.

The upregulation of TFEB may also be mediated by all-trans retinoic acid. All-trans retinoic acid may also be known as ATRA, retinoic acid, tretinoin, and vitamin A acid. All-trans retinoic acid may mediate upregulation of TFEB via the retinoid X receptor-α (RXR-α). During upregulation of TFEB, RXR-α forms a heterodimer with peroxisome proliferator-activated receptor-a (PPAR-α) and the RXR-α/PPAR-α heterodimer is recruited to the promoter of the Tfeb gene via a RXR binding site.

The composition mediating upregulation of TFEB may include a combination of the agent, for example, a lipid lowering drug, and all-trans retinoic acid or vitamin A. Such a combination may cooperatively mediate or enhance upregulation of TFEB as compared to administration of the agent or all-trans retinoic acid or vitamin A alone. The combination may cooperatively enhance upregulation of TFEB about 2-fold, about 3-fold, about 4-fold, about 5-fold, or about 10-fold as compared to administration of the lipid-lowering drug or all-trans retinoic acid or vitamin A alone. Particularly, the combination may cooperatively enhance upregulation of TFEB about 3-fold as compared to administration of the lipid-lowering drug or all-trans retinoic acid or vitamin A alone.

Another aspect of the present invention provides pharmaceutical compositions including at least one of the agents disclosed above. The pharmaceutical composition may also include all-trans retinoic acid or vitamin A. For example, the pharmaceutical composition may include gemfibrozil or a combination of gemfibrozil and all-trans retinoic acid or vitamin A or a combination of aspirin and all-trans retinoic acid or vitamin A.

The pharmaceutical compositions can be in the form of, for example, tablets, pills, dragees, hard and soft gel capsules, granules, pellets, aqueous, lipid, oily or other solutions, emulsions such as oil-in-water emulsions, liposomes, aqueous or oily suspensions, syrups, alixiers, solid emulsions, solid dispersions or dispersible powders. In pharmaceutical compositions for oral administration, the agent may be admixed with commonly known and used adjuvants and excipients, for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE). In the pharmaceutical composition, the agent may also be dispersed in a microparticle, e.g. a nanoparticulate, composition.

For parenteral administration, the agent or pharmaceutical compositions of the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration the agent or pharmaceutical compositions of the agent can be in the form of an aqueous, lipid, oily or other kind of solution or suspension or even administered in the form of liposomes or nano-suspensions.

Modes of Administration

The agents disclosed above or pharmaceutical compositions including these agents can be administered by any method that allows for the delivery of a therapeutic effective amount of the agent to the subject. Modes of administration can include, but are not limited to, oral, topical, transdermal and parenteral routes, as well as direct injection into a tissue, and delivery by a catheter. Parenteral routes can include, but are not limited to subcutaneous, intradermal, intra-articular, intravenous, intraperitoneal and intramuscular routes. In one embodiment, the route of administration is by topical or transdermal administration, such as by a lotion, cream, a patch, an injection, an implanted device, a graft or other controlled release carrier. Routes of administration include any route which directly delivers the composition to the systemic circulation (e.g., by injection), including any parenteral route.

One embodiment of the method of the present invention comprises administering at least one agent, for example gemfibrozil or a combination of gemfibrozil and ATRA, in a dose, concentration and for a time sufficient to prevent the development of, or to lessen the extent of, a LSD. Certain embodiments include administering systemically at least one agent in a dose between about 0.1 micrograms and about 100 milligrams per kilogram body weight of the subject, between about 0.1 micrograms and about 10 milligrams per kilogram body weight of the subject, between about 0.1 micrograms and about 1 milligram per kilogram body weight of the subject. In practicing this method, the agent or therapeutic composition containing the agent can be administered in a single daily dose or in multiple doses per day. This treatment method may require administration over extended periods of time. The amount per administered dose or the total amount administered will be determined by the physician and will depend on such factors as the mass of the patient, the age and general health of the patient and the tolerance of the patient to the compound.

Embodiments of the invention will be further described in the following examples, which do not limit the scope of the invention described in the claims.

EXAMPLES

Example 1—Materials and Methods

Reagents: DMEM/F-12 50/50 1×, Hank's balanced salt solution (HBSS) and 0.05% trypsin were purchased from Mediatech (Washington, DC). Fetal bovine serum (FBS) was obtained from Atlas Biologicals (Fort Collins, CO). Antibioticantimycotic, gemfibrozil and all trans retinoic acid (ATRA) were obtained from Sigma-Aldrich (St. Louis, MO).

Isolation of Primary Mouse Astroglia: Astroglia were isolated from mixed glial cultures as described (24, 25) according to the procedure of Giulian and Baker (26). Briefly, on day 9, the mixed glial cultures were washed three times with Dulbecco's modified Eagle's medium/F-12 and subjected to shaking at 240 rpm for 2 h at 37° C. on a rotary shaker to remove microglia. After 2 days, the shaking was repeated for 24 h for the removal of oligodendroglia and to ensure the complete removal of all nonastroglial cells. The attached cells were seeded onto new plates for further studies.

Isolation of Primary Mouse Neurons: Fetal (E18-E16) mouse neurons were prepared as previously described (27) with modifications. Whole brains were removed and the cells were washed by centrifugation three times at 1200 rpm for 10 min, the pellet dissociated and the cells plated at 10% confluence in 8-well chamber slides pre-treated for >2 hr with Poly-D-Lysine (Sigma, St. Louis, MO). After 4 min, the non-adherent cell suspension was aspirated and 500 ml complete Neurobasal media (Invitrogen) supplemented with 2% B27 was added to each well. The cells were incubated for 4 days prior to experimentation. Double-label immunofluorescence with β-tubulin and either GFAP or CD11b revealed that neurons were more than 98% pure (data not shown). The cells were stimulated with gemfibrozil in Neurobasal media supplemented with 2% B27 minus antioxidants (Invitrogen) for 24 hr prior to methanol fixation and immunostaining.

Semi-Quantitative Reverse Transcriptase-Coupled Polymerase Chain Reaction (RT-PCR): Total RNA was isolated from mouse primary astrocytes and human primary astrocytes using RNA-Easy Qiagen (Valencia, CA) kit following manufactures protocol. Semi-quantitative RTPCR was carried out as described earlier (28) using oligo (dT) 12-18 as primer and moloney murine leukemia virus reverse transcriptase (MMLV-RT, Invitrogen) in a 20 μl reaction mixture. The resulting cDNA was appropriately amplified using Promega Master Mix (Madison, WI) and the following primers (Invitrogen) for murine genes:

```
Mouse Tfeb:
Sense,
                               (SEQ ID NO.: 1)
5'-AAC AAA GGC ACC ATC CTC AA-3';

Antisense,
                               (SEQ ID NO.: 2)
5'-CAG CTC GGC CAT ATT CAC AC-3';

Mouse Lamp2:
Sense,
                               (SEQ ID NO.: 3)
5'-GGT GCT GGT CTT TCA GGC TTG ATT-3';

Antisense,
                               (SEQ ID NO.: 4)
5'-ACC ACC CAA TCT AAG AGC AGG ACT-3';

Mouse Limp2:
Sense,
                               (SEQ ID NO.: 5)
5'-TGT TGA AAC GGG AGA CAT CA-3';

Antisense,
                               (SEQ ID NO.: 6)
5'-TGG TGA CAA CCA AAG TCG TG-3';

Mouse Npc1:
Sense,
                               (SEQ ID NO.: 7)
5'-GGG ATG CCC GTG CCT GCA AT-3';

Antisense,
                               (SEQ ID NO.: 8)
5'-CTG GCA GCT ACA TGG CCC CG-3';

Mouse Gapdh:
Sense,
                               (SEQ ID NO.: 9)
5'-GCA CAG TCA AGG CCG AGA AT-3';

-continued
Antisense,
                              (SEQ ID NO.: 10)
5'-GCC TTC TCC ATG GTG GTG AA-3'.
```

Amplified products were electrophoresed on 2% agarose (Invitrogen) gels and visualized by ethidium bromide (Invitrogen) staining. Glyceraldehyde-3-phosphate dehydrogenase (Gapdh) mRNA was used as a loading control to ascertain that an equivalent amount of cDNA was synthesized from each sample.

Quantitative Real-Time PCR: The mRNA quantification was performed using the ABIPrism7700 sequence detection system (Applied Biosystems, Foster City, CA) using SYBR Select master mix (Applied Biosystems). The mRNA expression of the targeted genes was normalized to the level of Gapdh mRNA and data was processed by the ABI Sequence Detection System 1.6 software.

Immunostaining of Cells: Immunocytochemistry was performed as described earlier (29). Briefly, 8 well chamber slides containing mouse primary astrocytes, mouse neurons were cultured to 70-80% confluence were fixed with chilled Methanol (Fisher Scientific, Waltham, MA) overnight, followed by two brief rinses with filtered PBS. Samples were blocked with 2% BSA (Fisher Scientific) in PBS containing Tween 20 (Sigma) and Triton X-100 (Sigma) for 30 min and incubated at room temperature under shaking conditions for 2 hr in PBS containing the following anti-mouse primary antibodies: TFEB (1:1000; Abcam), GFAP, (1:1000; DAKO), LAMP2 (1:500, Abcam), NeuN (1:500, Millipore), and MAP2 (1:200, Millipore). After four 15 min washes in filtered PBS, the slides were further incubated with Cy2 or Cy5-labeled secondary antibodies (all 1:200; Jackson ImmunoResearch, West Grove, PA) for 1 hr under similar shaking conditions. Following four 15 minute washes with filtered PBS, cells were incubated for 4-5 min with 4', 6-diamidino-2-phenylindole (DAPI, 1:10,000; Sigma). The samples were run in an EtOH and Xylene (Fisher) gradient, mounted, and observed under Olympus BX41 fluorescence microscope.

Immunostaining of Tissue Sections: After 60 days of treatment, mice were sacrificed and their brains fixed, embedded, and processed. Sections were made from different brain regions and for immunofluorescence staining on fresh frozen sections, anti-mouse TFEB (1:500), anti-mouse LAMP2 (1:200) and anti-mouse NeuN (1:500) were used. The samples were mounted and observed under Olympus BX41 fluorescence microscope (30).

LysoTracker Staining: Fibroblasts cultured to 70-80% confluence were subjected to different stimuli under reduced serum (2%) DMEM medium followed by incubation with 75 nM LysoTracker Red DND99 (Invitrogen) for 45 mins. Cells were then washed thoroughly with filtered PBS and mounted on glass slides and viewed under BX41 fluorescence microscope Immunoblotting: Western blotting was conducted as described earlier (31, 32) with modifications. Briefly, cells were scraped in 1× RIPA buffer, protein was measured using Bradford reagent and sodium dodecyl sulfate (SDS) buffer was added and electrophoresed on NuPAGE® Novex® 4-12% Bis-Tris gels (Invitrogen) and proteins transferred onto a nitrocellulose membrane (Bio-Rad) using the Thermo-Pierce Fast Semi-Dry Blotter.

The membrane was then washed for 15 min in TBS plus Tween 20 (TBST) and blocked for 1 hr in TBST containing BSA. Next, membranes were incubated overnight at 4° C. under shaking conditions with the following 1° antibodies;

TFEB (1:1000, Abcam), LAMP2 (1:500, Abcam) and β-actin (1:800; Abcam, Cambridge, MA). The next day, membranes were washed in TBST for 1 hr, incubated in 2° antibodies against 1° antibody hosts (all 1:10,000; Jackson ImmunoResearch) for 1 hr at room temperature, washed for one more hour and visualized under the Odyssey® Infrared Imaging System (Li-COR, Lincoln, NE).

Construction of Mouse Tfeb Promoter-driven Reporter Construct: Mouse genomic DNA isolated from primary mouse astrocytes was used as the template during PCR. The 5' flanking sequence of the mouse TFEB (−916/+61) gene was isolated by PCR. Primers were designed from gene bank sequences. Tfeb: sense: 5'- acgcgt CCA GGA GCC AGG GAC GGG GTA CAT CTC -3' (SEQ ID NO.: 11); antisense: 5'- agatct AAG GAG AAA CTG AGT CCG GGC AGA AGG -3' (SEQ ID NO.: 12). The sense primer was tagged with an Mlu1 restriction enzyme site while the antisense primer was tagged with Bgl II. The PCR was performed using an Advantage-2 PCR kit (Clontech) according to the manufacturer's instruction. The resulting fragments were gel purified and ligated into the PGEM-TEasy vector (Promega). These fragments were further subcloned into the PGL-3 Enhancer vector after digestion with corresponding restriction enzymes and verification by sequencing ACGT Inc. DNA Sequencing Services.

Cloning of Tfeb Promoter and Site-Directed Mutagenesis: Site-directed mutagenesis was done by using the site directed mutagenesis kit (Stratagene, USA). Two primers in opposite orientation were used to amplify the mutated plasmid in a single PCR reaction. The primer sequence for mutated promoter site were: Mutated: Sense: 5'-GCA ACA GCA AGT GCG GAT TTG AGG GGG GGG GAC GGT GGG-3' (SEQ ID NO.: 13); Antisense :5'-CCC ACC GTC CCC CCC CCT CAA ATC CGC ACT TGC TGT TGC-3' (SEQ ID NO.: 14). The PCR product was precipitated with ethanol and then phosphorylated by T4 kinase. The phosphorylated fragment was self-ligated by T4 DNA ligase and digested with restriction enzyme DpnI to eliminate the non-mutated template. The mutated plasmid was cloned and amplified in *Escherichia coli* (DH5-α strain) competent cells.

Assay of Tfeb Promoter-driven Reporter Activity: Cells plated at 50-60% confluence in 12-well plates were cotransfected with 0.25 μg of pTFEB(WT)-Luc, pTFEB(Mu)-Luc and using Lipofectamine Plus (Invitrogen). After 24 h of transfection, cells were stimulated with different agents under serum free conditions for 6 h. Firefly luciferase activities were analyzed in cell extracts using the Luciferase Assay System kit (Promega) in a TD-20/20 Luminometer (Turner Designs) as described earlier (33, 34).

Chromatin Immunoprecipitation Assay: ChIP assays were performed using method described by Nelson et al (35), with certain modifications. Briefly, mouse primary astrocytes were stimulated by 10 μM gemfibrozil and 0.5 μM RA together for 6 hrs followed by fixing with formaldehyde (1.42% final volume) and quenching with 125 mM Glycine. The cells were pelleted and lysed in IP buffer containing 150 mM NaCl, 50 mM Tris-HCl (pH 7.5), 5 mM EDTA, NP-40 (0.5% vol/vol), Triton X-100 (1.0% vol/vol). For 500 ml, add 4.383 g NaCl, 25 ml of 100 mM EDTA (pH 8.0), 25 ml of 1 M Tris-HCl (pH 7.5), 25 ml of 10% (vol/vol) NP-40 and 50 ml of 10% (vol/vol) Triton X-100 containing the following inhibitors; 10 μg/ml leupeptin, 0.5 mM phenylmethylsulfonyl fluoride (PMSF), 30 mM p-nitrophenyl phosphate, 10 mM NaF, 0.1 mM Na3VO4, 0.1 mM Na2MoO4 and 10 mM β-glycerophosphate.

After one wash with 1.0 ml IP buffer the pellet was resuspended in 1 ml IP buffer (containing all inhibitors) and sonicated and sheared chromatin was split into two fractions (one to be used as Input). The remaining fraction was incubated overnight under rotation at 4° C. with 5-7 μg of anti- PPARα or anti-RXRα Abs or anti-PGC1α or RNA Pol or normal IgG (Santa Cruz) followed by incubation with Protein G-Agarose (Santa Cruz) for 2 hrs at 4 oC under rotation. Beads were then washed five times with cold IP buffer and a total of 100 μl of 10% Chelex (10 g/100 ml H2O) was added directly to the washed protein G beads and vortexed. After 10 min boiling, the Chelex/protein G bead suspension was allowed to cool to room temperature. Proteinase K (100 μg/ml) was then added and beads were incubated for 30 min at 55° C. while shaking, followed by another round of boiling for 10 min. The suspension was centrifuged and supernatant collected. The Chelex/protein G beads fraction was vortexed with another 100 μl water, centrifuged again, and the first and the second supernatants were combined. Eluate was used directly as a template in PCR.

The following primers were used to amplify fragments flanking RXR binding element in the mouse Tfeb promoter: Set1: sense: 5'-GAA CAT TCC AGG TGG AGG CA-3' (SEQ ID NO.: 15), antisense: 5'-CCC CCA ACA CAT GCT TCT CT-3' (SEQ ID NO.: 16); Set2: sense: 5'-GAG TCT CTC GGA GGA GGT GA-3' (SEQ ID NO.: 17), antisense: 5'-ACT CCA GGC ATG CTT TCT CC-3'(SEQ ID NO.: 18). The PCRs were repeated by using varying cycle numbers and different amounts of templates to ensure that results were in the linear range of PCR. The qRT-PCR was performed using the same primers and SYBR select mastermix. Data were normalized to input and non-specific IgG and fold increase vs control was calculated.

Densitometric Analysis: Protein blots were analyzed using ImageJ (NIH, Bethesda, Md.) and bands were normalized to their respective β-actin loading controls. Data are representative of the average fold change with respect to control for at least 25 different images per condition from three independent set of experiments.

Statistics: Values are expressed as means ±SEM of at least three independent experiments. Statistical analyses for differences were performed via Student's T-test. This criterion for statistical significance was p<0.05.

Example 2—Activation of PPARα and RXRα Induces Expression of TFEB in Mouse Primary Brain Cells PPAR activators, like the FDA-approved drug gemfibrozil, where examined to determine if they could upregulate the expression of TFEB in mouse brain cells. Since it has been known that PPARα and RXRα forms a transcriptionally active complex (21, 36, 37), we used both gemfibrozil and ATRA, which activates RXRα , to check if there is any additive effect due to dual treatment. Mouse primary astrocytes (MPA) were treated in serum free media with single doses of gemfibrozil and ATRA and also in combination. Quantitative realtime PCR data showed increased expression of Tfeb in all three groups with the increase being marginally higher in combinatorial treatment (but not statistically significant w.r.t individual treatments) (FIG. 1A). When a combination of both gemfibrozil and ATRA was used, we could achieve similar level expression of Tfeb at much lower doses of both the compounds (10 μM and 0.2 μM respectively) compared to 25 μM of gemfibrozil and 0.5 μM of ATRA. The time point analysis with the combinatorial treatment showed that the Tfeb expression could be induced as early as 6 hrs. up to 24 hrs. (FIG. 1D). The qRT-PCR data for both dose and time were validated by western blots, which showed a similar pattern of increase in TFEB levels (FIGS. 1B, 1C, 1E & 1F).

Furthermore, we used mouse primary astrocytes and primary neurons and treated them with the combination of gemfibrozil and ATRA in serum free media for 24 hrs and performed immunocytochemistry. The data showed a distinct increase in the levels of TFEB in both astrocytes and neurons as well as localization of TFEB in and around the nucleus (FIGS. 1G & 1I). The TFEB immunoreactivity was quantified using ImageJ and we observed ~4-fold increase in the overall levels of TFEB and ~5-6-fold increase of TFEB localization of TFEB in the nucleus upon treatment (FIGS. 1H & 1J) It has been previously shown that starvation and nutrient deficiency leads to activation of TFEB, so in this study all the untreated cells were maintained in serum free conditions for the whole duration of the treatment as well, so that the baseline change in the levels of TFEB would remain the same between the groups.

Example 3—PPARα and RXRα are Involved in the Drug Mediated Upregulation of TFEB

Figure 2:
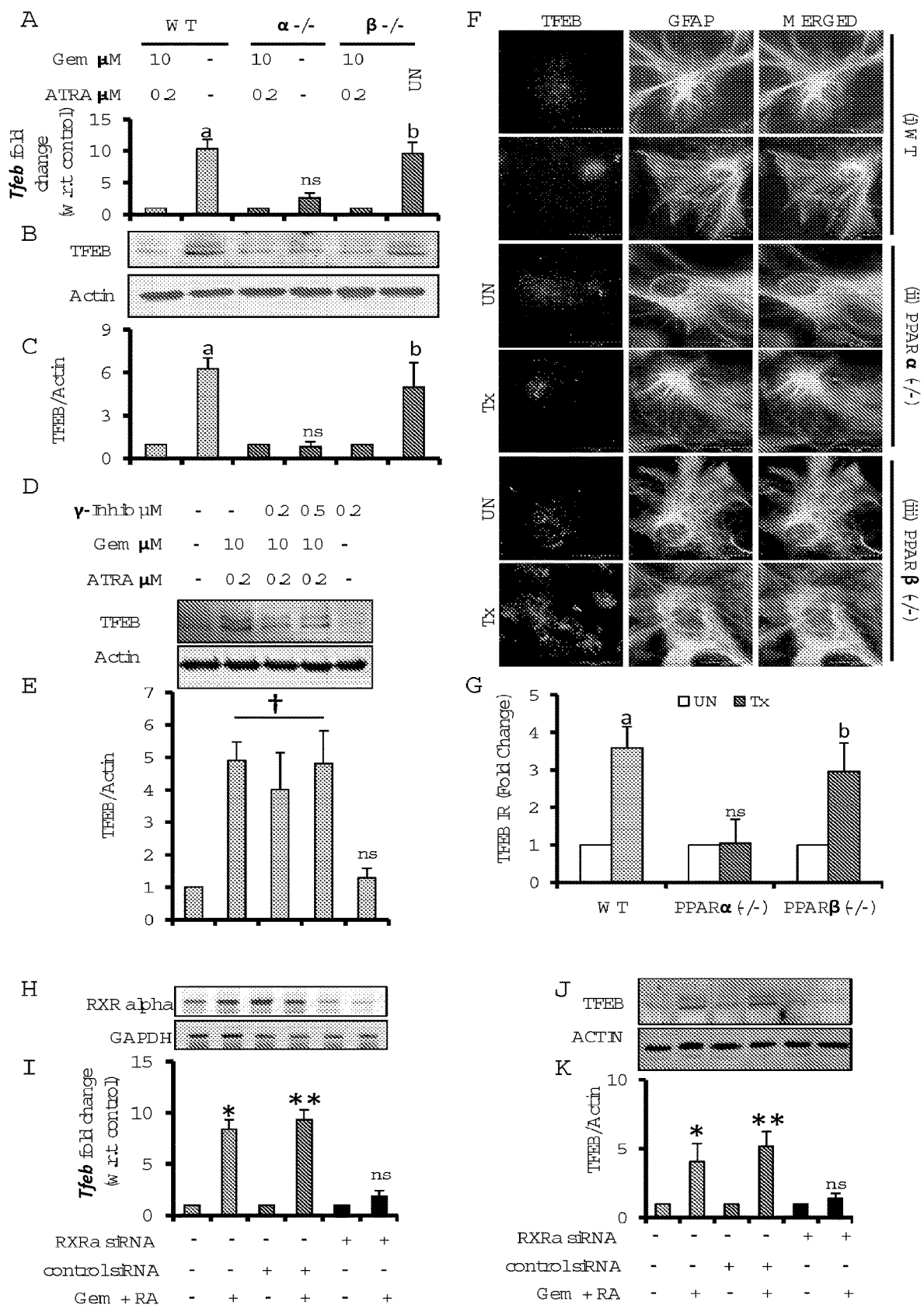
FIG. 2 shows involvement of PPARα and RXRα in fibrate drug-mediated upregulation of TFEB mRNA and protein: (A, B) Mouse primary astrocytes isolated from PPARα-/- and PPARβ-/- and wild type mouse were treated with combination of gemfibrozil (10 μM) and retinoic acid (0.2 μM) in serum free DMEM/F12 for 24 hrs followed by monitoring the mRNA expression of Tfeb by real-time PCR (A) and protein level of TFEB by immunoblot (B). (C) Densitometric analysis of TFEB levels (relative to β-Actin) in PPARα-/- and PPARβ-/- and wild type astrocytes. pa<0.05 vs WT control; pb<0.05 vs PPARβ-/- control; ns—not significant w.r.t PPARα-/- control. (D) Mouse primary astrocytes isolated from WT mice were pre-treated with GW9662 for 30 min followed by treatment with gemfibrozil and retinoic acid under similar culture conditions followed by monitoring the levels of TFEB protein expression by immunoblot. (E) Densitometric analysis of immunoblot for TFEB (relative to β-Actin) p†<0.05 vs control; ns—not significant w.r.t control. (F) Mouse primary astrocytes isolated from PPARα-/- and PPARβ-/- and WT mice were treated with 10 μM gemfibrozil and 0.2 μM retinoic acid in serum free DMEM/F12 for 24 hrs and double-labeled for TFEB (red) and GFAP (green). DAPI was used to stain nuclei. UN—No treatment. Scale bar=20 μM. (G) Quantification of TFEB immunoreactivity (TFEB IR) for mouse primary astrocytes calculated as fold over control. At least 25 separate images per condition from three independent set of experiments are quantified using ImageJ. pa<0.05 vs WT control; pb<0.05 vs PPARβ-/- control; ns—not significant w.r.t PPARα-/- control. (H, I, J) Mouse primary astrocytes were untransfected, transfected with scrambled siRNA (1.0 μg) or RXRα siRNA (1.0 μg) for 36 hrs followed by treatment with RA (0.2 μM) and gemfibrozil (10 μM) in combination for 24 hrs serum free DMEM/F12 medium followed by RT-PCR for RXRα to check the level of gene silencing (H) and quantitative real time PCR for TFEB (J) and immunoblot for TFEB (J). (K) Denistometric analysis of immunoblot for TFEB (relative to β actin). p*<0.05 vs untransfected control; p**<0.05 vs scrambled siRNA transfected control; ns—not significant w.r.t. RXR-α siRNA transfected control. All results are representative of or mean ±SEM of at least three independent set of experiments.

The hypothesis that PPARα in conjunction with RXRα could be involved in the drug mediated upregulation of TFEB was tested by using mouse primary astrocytes from PPARα (−/−) animals and knocking down RXRα in WT mouse primary astrocytes. MPA obtained from WT, PPARα (−/−) and PPARβ (−/−) animals were treated under similar conditions as above and checked for the mRNA and protein expression of TFEB. Both real-time PCR and western blots for TFEB showed that TFEB could be upregulated in WT and PPARβ (−/−) astrocytes but not at the same level in PPARα (−/−) astrocytes (FIGS. 2A, 2B & 2C). The findings were further confirmed by immunocytochemistry where we observed almost 3-4-fold increase in TFEB levels in WT and PPARβ (−/−) but not in PPARα (−/−) (FIGS. 2F & 2G).

It was reported that PPARγ coactivator-1a (PGC1A) could be involved in transcriptionally activating Tfeb, so we tested whether PPARγ is involved in this particular drug mediated expression of TFEB by using PPARγ inhibitors. Western blot for TFEB using pretreatment with PPARγ specific inhibitors prior to treatment with the drugs indicate that gemfibrozil and ATRA may not be using the PPARγ mediated pathway for the upregulation of TFEB (FIGS. 2D & 2E). PPARα and RXRα have been known to form a transcriptional complex and our data showed marginal increase of TFEB in presence of ATRA. We wanted to see whether ATRA exerts its effects via RXRα. WT MPAs were treated with RXRα specific siRNA followed by treatment with the combination of gemfibrozil and ATRA and both mRNA and protein analyses were performed. The data showed a successful knockdown of RXRα gene and consequently the effect of drugs were partially abrogated in absence of RXRα, which was evident from the levels of Tfeb mRNA after RXRα silencing (FIGS. 2H & 2I). The western blot also showed similar results with the TEFB levels being significantly less in RXRα silenced cells compared to scrambled siRNA after treatment (FIGS. 2J & 2K). Taken together these data indicate that PPARα and RXRα could be involved in the upregulation of TFEB by gemfibrozil and ATRA.

Figure 3:
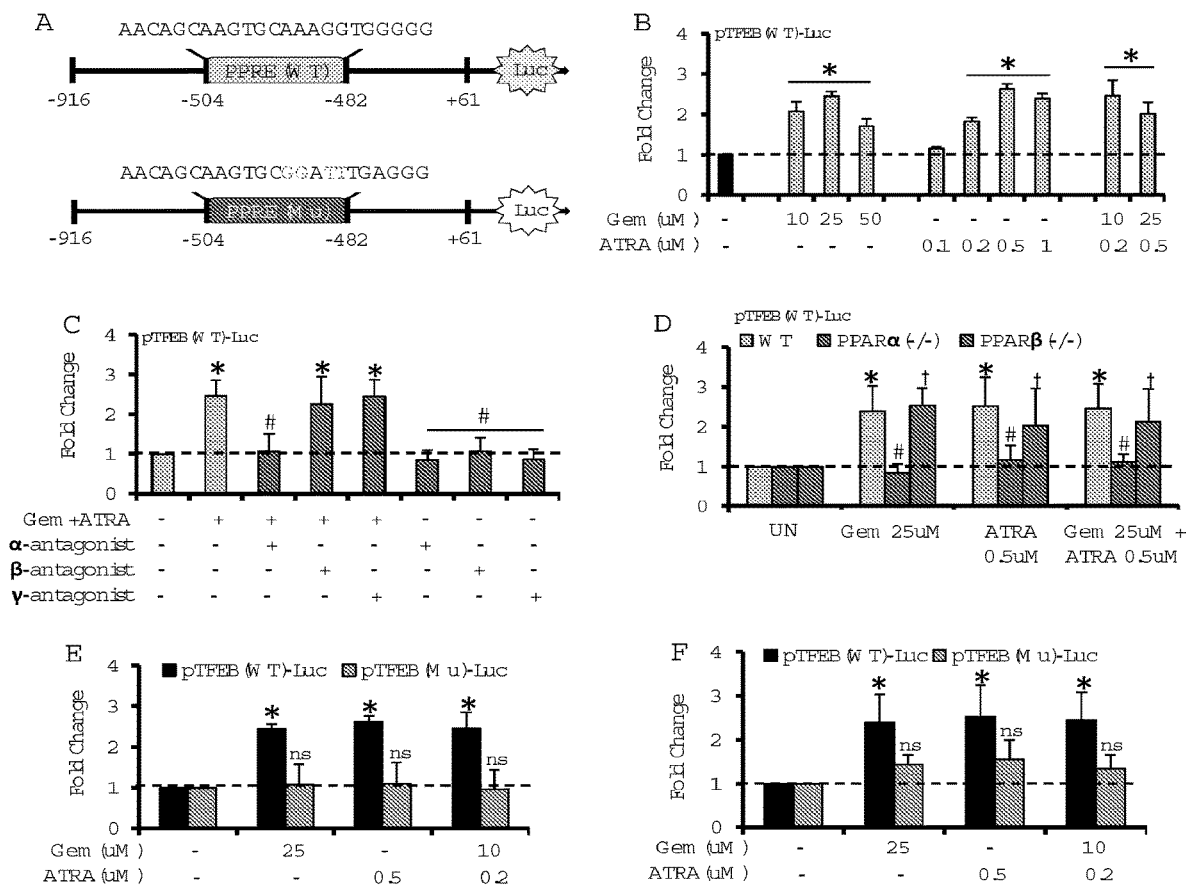
FIG. 3 shows PPARα transcriptionally regulating TFEB expression under treatment condition: (A) Map of wild-type and mutated PPRE site of TFEB-Luciferase promoter constructs. (B) BV2 cells were transfected with pTFEB(WT)-Luc for 24 hrs followed by treatment with different concentrations of gemfibrozil and retinoic acid alone and in combination and subjected to luciferase assay. p*<0.05 vs untreated control. (C) BV2 cells were transfected with pTFEB(WT)-Luc for 24 hrs followed by pretreatment with PPARα-, PPARβ-, PPARγ-antagonists followed by treatment with gemfibrozil and retinoic acid and subjected to luciferase assay. p*<0.05 vs untreated control. p #<0.05 vs treatment. (D) Mouse primary astrocytes isolated from PPARα-/- (center) and PPARβ-/- (right) and wild type (left) mouse were transfected with pTFEB(WT)-Luc for 24 hrs followed by treatment with gemfibrozil and retinoic acid and subjected to luciferase assay. p*<0.05 vs untreated WT control. . p #—not significant vs untreated PPARα-/- control . . . p†<0.05 vs untreated PPARβ-/- control. (E, F) BV2 cells (E) and mouse primary astrocytes (F) were transfected with pTFEB(WT)-Luc and pTFEB(Mu)-Luc for 24 hrs followed by treatment with gemfibrozil and retinoic acid and subjected to luciferase assay. p*<0.05 vs untreated pTFEB (WT)-Luc transfected control. ns—not significant w.r.t. untreated pTFEB(Mu)-Luc transfected control. All results are mean ±SEM of at least six sets of independent experiments.

Example 4—PPARα/RXRα Heterodimer Transcriptionally Regulate TFEB Expression Under Treatment Condition PPARα and RXRα together form a transcriptional complex, so having determined that those receptors appear to upregulate Tfeb, we tested whether the receptors transcriptionally regulate Tfeb expression. After analysis of the promoter site of Tfeb, we found the presence of a Peroxisomal Proliferator Response Element (PPRE) about 480 bp upstream to the transcription start site (TSS) of Tfeb. The Tfeb promoter (pTFEB(WT)) containing the PERO was cloned into the pGL3 Enhancer vector. We also mutated the core sequence of the PPRE and the mutated promoter construct (pTFEB(Mu)) was also cloned into PGL3 vector. The Wild type luciferase construct, when transfected into BV2 cells showed marked increase in the luciferase activity (FIG. 3B). When the cells containing the pTFEB(WT) luciferase construct were treated with PPARα-antagonist (GW6471; 250 nM), PPARβ-antagonist (GSK0660; 250 nM), PPARγ-antagonist (GW9662; 5 nM) we observed the luciferase activity was similar to the untreated cells in PPARα antagonist treated cells, but not in the PPARβ- or PPARγ-antagonist treated cells (FIG. 3C).

In mouse primary astrocytes isolated from WT, PPARα (−/−) and PPARβ (−/−) animals, we observed increased luciferase activity in WT and PPARβ (−/−) cells but not in PPARα (−/−) (FIG. 3D). Furthermore, when the construct with mutated PPRE site (pTFEB(Mu)-Luc) was transfected into BV2 and mouse primary astrocytes we found a dramatic decrease in the luciferase activity in cells containing the mutant construct (FIGS. 3E & 3F). Taken together, these data indicates that the activation of PPARα plays an important role in the induction of Tfeb upon treatment with gemfibrozil and retinoic acid.

Figure 4:
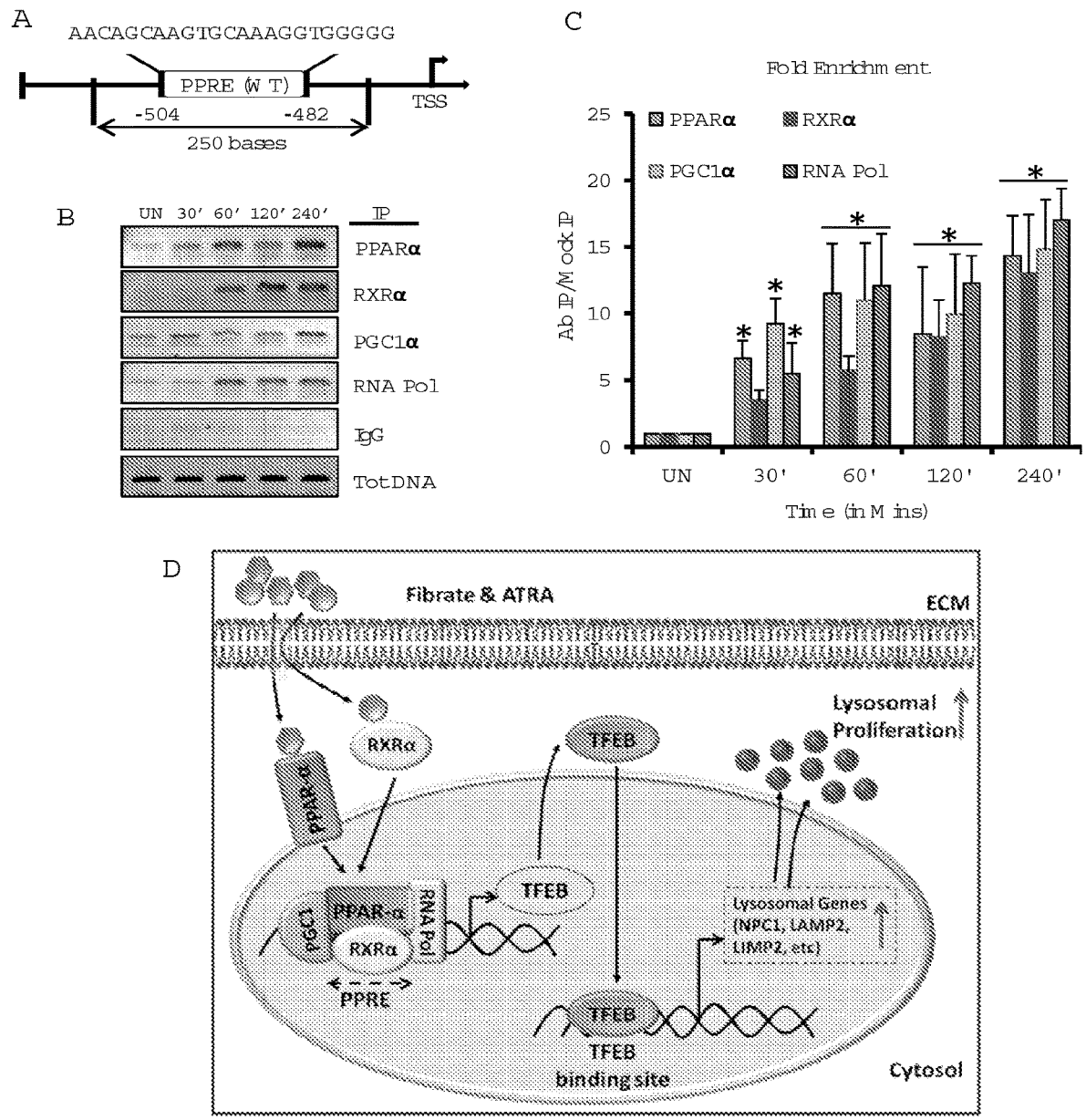
FIG. 4 shows tranpcriptional activation of TFEB by PPARα-RXRα-PGC1α complex (A) Map of PPRE on TFEB promoter with core sequence and amplicon length for ChIP. (B,C) Mouse astrocytes were treated with the combination of gemfibrozil (10 μM) and RA (0.2 μM) for 30, 60, 120 and 240 mins and recruitment of PPARα (far left), RXRα (center left), PGC1α (center right) and RNA Polymerase (far right) on the PPRE binding site of Tfeb promoter was monitored by ChIP followed by RT-PCR (B) and qRT-PCR (C). Normal IgG was used as control. p*<0.05 vs untreated control. All results are representative of or mean ±SEM at least there independent sets of experiments. (D) Schematic representation of induction of lysosomal biogenesis by activating peroxisomal proliferators.

Finally, we decided to investigate the actual DNA binding role of PPARα on the Tfeb promoter in this context. It has been shown that upon activation PPARα, RXRα and PGC1α forms a complex which initiates transcriptional activation of many genes (38-42); we investigated whether that is the case here. Mouse primary astrocytes treated with gemfibrozil and retinoic acid for different time points from 30 mins to 240 mins were subjected to ChIP analysis by immunoprecipitating the chromatin fragments with anti-PPARα, -RXRα and -PGC1α antibodies and anti-RNA Pol and normal IgG were kept as controls. Both the semi-quantitative PCR and quantitative RT-PCR showed an increased enrichment of the amplicon over time with the pulldown by the specific antibodies (FIGS. 4B & 4C). Immunoprecipation followed by PCR with normal IgG showed almost undetectable bands in RT-PCR and PCR with total fragmented DNA showed uniform signal in RT PCR, showing the uniformity and specificity of the results. In realtime PCR, the Ct values were normalized to % input and further normalized with IgG signal to get a signal over noise value, to verify the specificity of the results. The experiments were repeated at least three times under same condition and cycles and dilution of PCR products were adjusted to ensure that the data were in the linear range of the PCR. All these findings so far indicate that activation of the PPARα and RXRα receptor directly can in fact transcriptionally regulate the expression Tfeb.

Example 5—Upregulation of TFEB Leads to Increased Lysosomal Biogenesis

Figure 5:
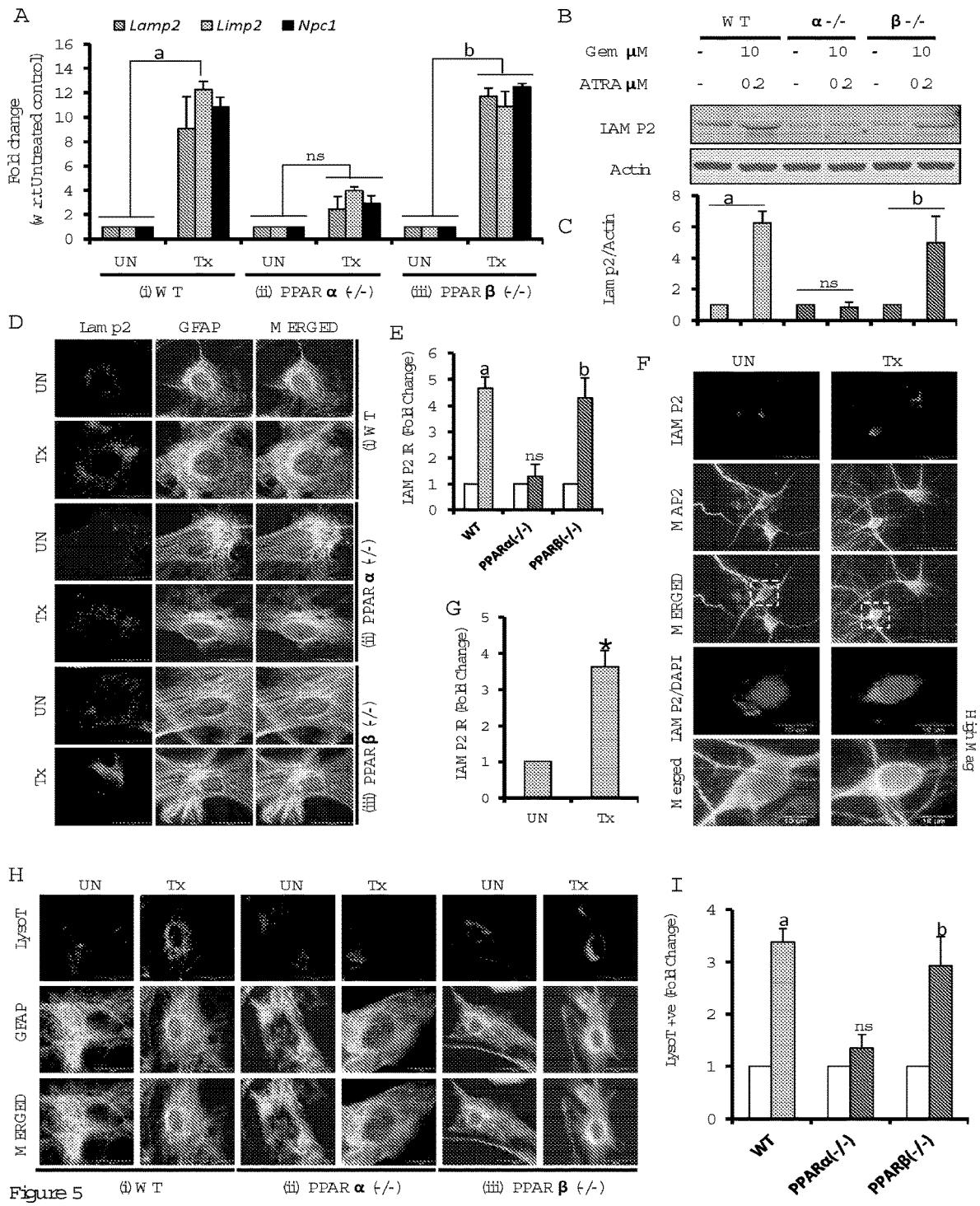
FIG. 5 shows PPARα dependant upregulation of TFEB inducing lysosomal biogenesis: (A, B) Mouse primary astrocytes isolated from PPARα-/- and PPARβ-/- and wild type mouse were treated with combination of gemfibrozil (10 μM) and retinoic acid (0.2 μM) in serum free DMEM/F12 for 24 hrs followed by monitoring the mRNA expression of lysosomal genes (Lamp2 (left), Limp2 (center), Npc1 (right)) by real-time PCR (A) and protein level of LAMP2 by immunoblot (B). (C) Densitometric analysis of LAMP2 levels (relative to β-Actin) in PPARα-/- and PPARβ-/- and wild type astrocytes. pa<0.05 vs WT control; pb<0.05 vs PPARβ-/- control; ns—not significant w.r.t PPARα-/- control. All results are representative of or mean ±SEM at least there independent sets of experiments. (D) Mouse primary astrocytes isolated from PPARα-/- and PPARβ-/- and WT mice were treated with 10 μM gemfibrozil and 0.2 μM retinoic acid in serum free DMEM/F12 for 24 hrs and double-labeled for LAMP2 (red) and GFAP (green). DAPI was used to stain nuclei. (E) Quantification of LAMP2 immunoreactivity (Lamp2 IR) for mouse primary astrocytes calculated as fold over control. pa<0.05 vs WT control; pb<0.05 vs PPARβ-/- control; ns—not significant w.r.t PPARα-/- control. (F) Mouse primary neurons isolated from WT mice were treated with 10 μM gemfibrozil and 0.2 μM retinoic acid in serum free DMEM/F12 for 24 hrs and double-labeled for LAMP2 (red) and Map2 (green). DAPI was used to stain nuclei. (G) Quantification of LAMP2 immunoreactivity (Lamp2 IR) for mouse primary neurons calculated as fold over control. p*<0.05 vs untreated control. (H) Mouse primary astrocytes isolated from PPARα-/- and PPARβ-/- and WT mice were treated with 10 μM gemfibrozil and 0.2 μM retinoic acid in serum free DMEM/F12 for 24 hrs and double-labeled for LysoTracker Red (red) and GFAP (green). (I) Quantification of LAMP2 immunoreactivity (Lamp2 IR) for mouse primary astrocytes calculated as fold over control. pa<0.05 vs WT control; pb<0.05 vs PPARβ-/- control; ns—not significant w.r.t PPARα-/- control. UN—No treatment. Scale bar=20 μm (for D, E & F), scale bar=10 μm for High Magnification Images (for E). AT least 25 images per condition from three different sets of experiments were analyzed for all image quantification data using ImageJ.

TFEB is the master regulator of lysosomal gene expression and biogenesis (9,12,16) so we expected an increase in the biogenesis and lysosomal markers with the upregulation of TFEB. The MPAs treated under the same condition were subjected to mRNA analysis for some lysosomal markers like Lamp2, Limp2 and Npc1. As expected the data showed elevated levels of those genes under treatment conditions in WT and PPARβ (−/−) cells, but not in PPARα (−/−) cells. (FIG. 5A) Western blot analysis and immunocytochemistry for LAMP2 in WT and K.O. cells showed a similar protein expression pattern as well (FIGS. 5B, 5C & 5D). The increase in levels of LAMP2 was also observed in mouse primary neurons (FIG. 5E). Furthermore, when cells were stained with LysoTracker Red we observed increased lysosome content per cell in the case of drug treated WT and PPARβ (−/−) cells but not PPARα (−/−) (FIG. 5F) which is consistent with our previous findings for TFEB and other lysosomal markers. These data suggest that gemfibrozil and ATRA can induce TFEB expression via PPARα/RXRα pathway which eventually leads to increased lysosomal biogenesis.

Figure 6:
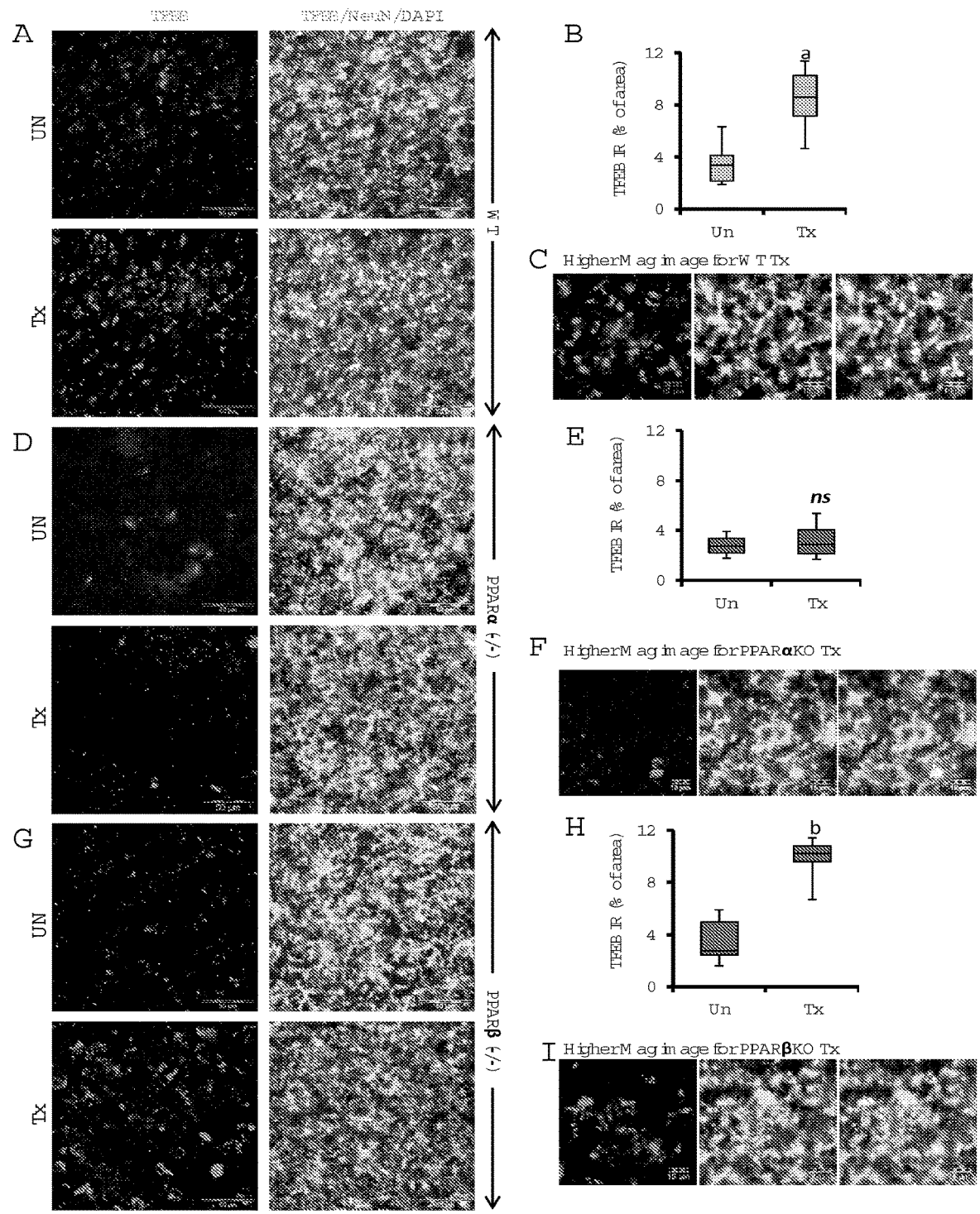
FIG. 6 shows that oral administration of gemfibrozil upregulates TFEB in vivo in the cortex of WT and PPARβ−/−, but not PPARα−/− mice: (A, D, G) WT, PPARα−/− and PPARβ−/− mice (n=6 in each group) were treated with 7.5 mg/kg body wt/day gemfibrozil and 0.1 mg/kg body weight of All-trans retinoic acid (dissolved in 0.1% methylcellulose) or vehicle (0.1% methylcellulose) via gavage. After 60 d of treatment, mice were killed and cortical sections were double labeled for TFEB (red) and NeuN (green). DAPI was used to visualize nucleus (C, F, I) Higher magnification images showing localization of TFEB and NeuN in the cortical neuron of mice from the treatment group (WT, PPARα−/− and PPARβ−/−). (B, E, H) Quantification of TFEB Immunoreactivity (TFEB IR) in untreated and treated samples from each group (WT, PPARα−/− and PPARβ−/−) expressed as percentage of area. pa<0.05 vs WT control; pb<0.05 vs PPARβ−/− control; ns—not significant w.r.t PPARα−/− control. At least 12 sections from each group (2 sections per animal) were quantified using ImageJ. Scale bar=50 μM and 10 μm (for higher magnification images).

Example 6—Agonists of PPARα and RXRα Induce Lysosomal Biogenesis In Vivo in the CNS of WT and PPARβ/−, but Not in PPARα−/−, Mice Once the involvement of PPARα was confirmed in the fibrate mediated upregulation of TFEB, we further checked whether the same results could be replicated in in vivo settings. WT, PPARα (−/−) and PPARβ (−/−) mice from same background were treated orally for 60 days with 7.5 mg/kg body wt/day gemfibrozil and 0.1 mg/kg body weight of ATRA dissolved in 0.1% methylcellulose, which was also used as vehicle. At the end of the treatment, the mice were sacrificed and cerebral cortex was sectioned, and immunofluorescence was performed for the presence of TFEB. This in vivo immunohistochemistry data validated our cell culture findings as we did not observe any remarkable elevation in the levels of TFEB in the cortex of PPARα (−/−) treated animals compared to vehicle controls, but a considerable response was observed in WT and PPARβ (−/−) animals (FIGS. 6A, 6D & 6G).

Figure 7:
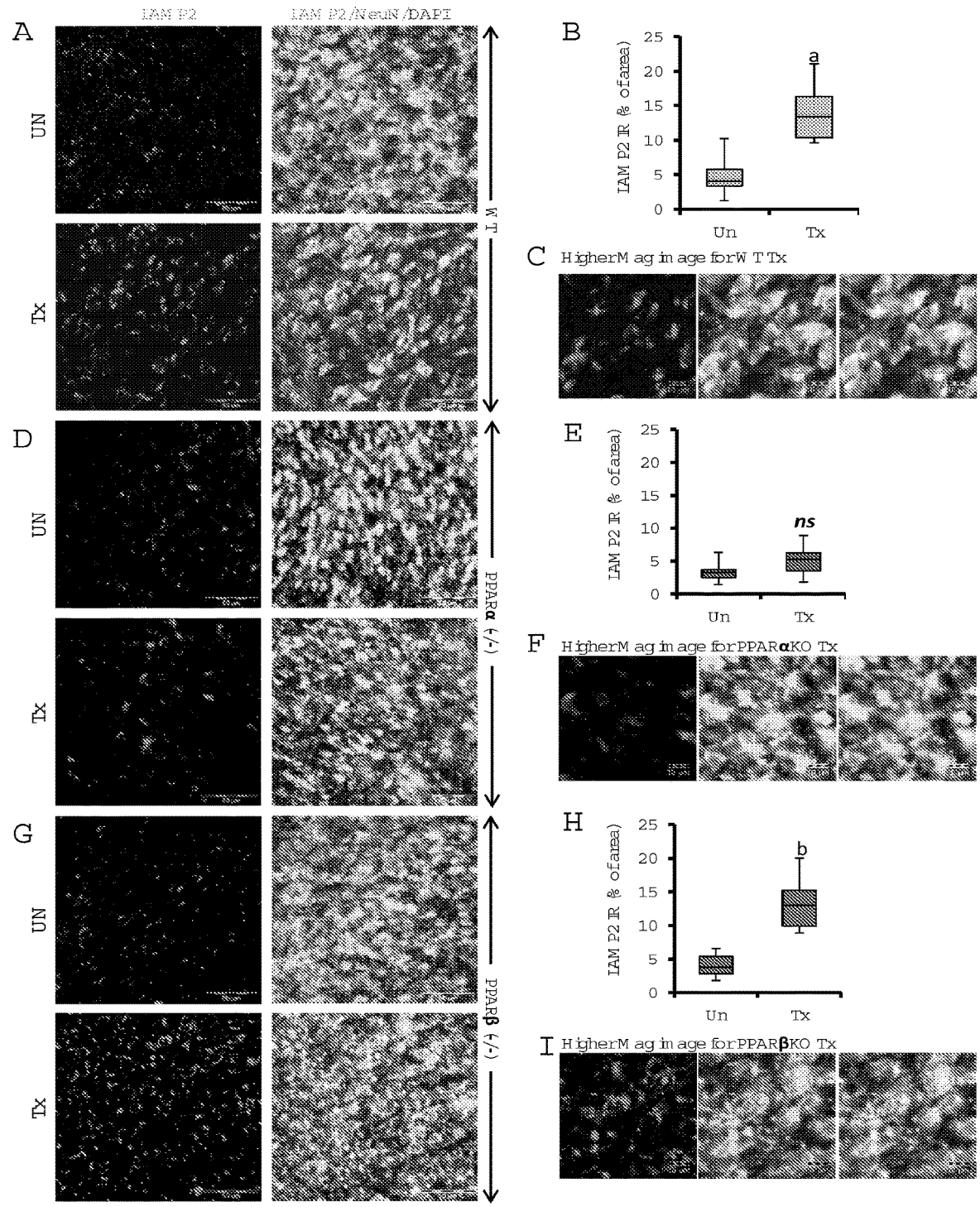
FIG. 7 shows that oral administration of gemfibrozil upregulates LAMP2 in vivo in the cortex of WT and PPARβ−/−, but not PPARα−/− mice: (A, D, G) WT, PPARα−/− and PPARβ−/− mice (n=6 in each group) were treated with 7.5 mg/kg body wt/day gemfibrozil and 0.1 mg/kg body weight of All-trans retinoic acid (dissolved in 0.1% methylcellulose) or vehicle (0.1% methylcellulose) via gavage. After 60 d of treatment, mice were killed and cortical sections were double labeled for LAMP2 (red) and NeuN (green). DAPI was used to visualize nucleus (C, F, I) Higher magnification images showing localization of LAMP2 and NeuN in the cortical neuron of mice from the treatment group (WT, PPARα−/− and PPARβ−/−). (B, E, I) Quantification of LAMP2 Immunoreactivity (LAMP2 IR) in untreated and treated samples from each group (WT, PPARα−/− and PPARβ−/−) expressed as percentage of area. pa<0.05 vs WT control; pb<0.05 vs PPARβ−/− control; ns—not significant w.r.t PPARα−/− control. At least 12 sections from each group (2 sections per animal) were quantified using ImageJ. Scale bar=50 μM and 10 μm (for higher magnification images).

We further quantified the TFEB positive signals in at least twelve sections per group and the values were represented as percentage of total area. The quantitative analysis confirmed a significant increase in TFEB positive signals in WT and PPARβ (−/−) animals, but not PPARα (−/−) animals (FIGS. 6B, 6E & 6H). Other sections of the cortex from the same animals were subjected to immunohistochemistry for the presence of LAMP2. The results indicate increased LAMP2 immunoreactivity in WT and PPARβ (−/−) animals, but not PPARα (−/−) animals (FIGS. 7A, 7D & 7G). The quantitative data also suggested a significant increase in LAMP2 positive signals in WT and PPARβ (−/−), but not PPARα (−/−), animals (FIGS. 7B, 7E & 7H).

Figure 8:
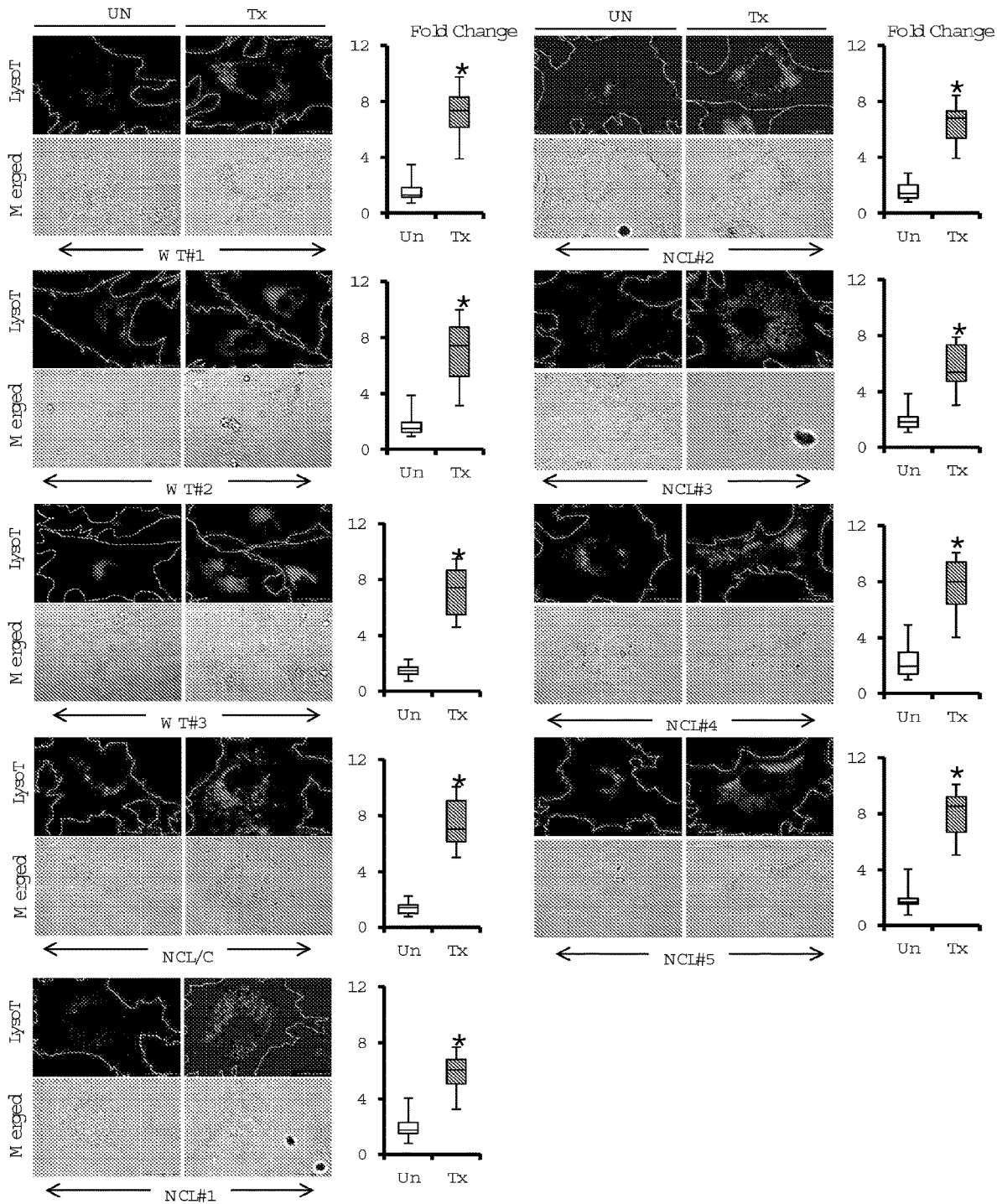
FIG. 8 shows that upregulation of TFEB induces lysosomal biogenesis in both normal and LINCL patient fibroblasts: Fibroblasts from healthy individuals (WT #1-3) and LINCL patients (NCL #1-5) and carrier of LINCL (NCL/C) were treated with gemfibrozil (10 μM) and retinoic acid (0.2 μM) in reduced serum (2%) DMEM medium for 24 hrs followed by staining with LysoTracker Red (red). Brightfield microscopy used for detecting cell morphology. Scale bar=20 μM. Corresponding box plots represent fold change in the LysoTracker positive signals in treated group vs control in each cell type. p*<0.05 vs untreated control. ROI—white dotted lines, represent area of the cell. Fold change calculated as LysoT +ve signal per unit area per cell in treatment vs control. At least 25 individual images per condition per cell type were quantified using ImageJ.

Example 7—Gemfibrozil and ATRA Induced Lysosomal Biogenesis in Fibroblasts of LINCL Patients In order to test whether similar results could be replicated in patient cells, we obtained skin fibroblasts from normal and LINCL affected patients and treated the cells with similar concentrations of gemfibrozil and ATRA in reduced serum media (2% serum). To account for any change resulting due to serum starvation the untreated controls were kept in similar serum condition for the length of the treatment (24 hrs). After that the fibroblasts were stained with LysoTracker Red and we observed similar pattern of increased lysosome accumulation in the cells across the board. Normal fibroblasts (WT #1 through WT #3) and fibroblasts from LINCL patients carrying Cln2 mutations (NCL #1 through NCL #5) as well as LINCL carrier (NCL/C) fibroblasts showed similar increase in lysosome per cell (FIG. 8). To normalize for the number and size of cells in the images, we calculated the LysoTracker +ve signals per unit area per cell and then performed a fold over control analysis. At least 25 fields per group were analyzed for LysoTracker positive signals and the data suggested a significant increase in all fibroblasts irrespective of the disease status, although the basal level of lysosomes in the cell and level of increase varied from cell to cell. This data suggest that the effect of the treatment is independent of the disease condition for LINCL patients.

Example 8—Discussion of Examples 2 to 7

Lysosomes are one of the major organelles in cells that not only act as the waste management machinery of the cell but also play significant roles in other biological processes like antigen presentation, regulation of certain hormones, bone remodeling, necrotic cell death, cell surface repair, and developmental and other signaling pathways (2, 43-47). In order to carry out these varied functions the biogenesis and activity of lysosomes needs to be tightly regulated. According to recent findings, TFEB is a master regulator of lysosomal biogenesis (9, 12, 15). Over the years different groups have underscored the role of lysosome in different disease scenarios (48-53). Lysosome-related genes are reported to be closely regulated in the orbital fat of patients suffering from Graves' ophthalmopathy whereas downregulation of lysosomal processing improved pegylated lipopolyplex-mediated gene transfection (53, 54). The increase in lysosomal biogenesis may not necessarily prove to be beneficial in all disease and cell types, but in some cases induction of the autophagy-lysosomal pathway could be helpful for cellular clearance of toxic wastes (55, 56).

Over the past few years TFEB has emerged as a potential therapeutic target for some lysosome-related diseases. Taiji Tsunemi et al reported that by activating transcription factor EB (TFEB) via PGC1α could result in increased htt turnover and the elimination of protein aggregates (57,58). There are reports suggesting a link between α-synuclein toxcitiy and impaired function of TFEB and identified TFEB as a target for neuroprotective therapy in PD (59). TFEB activation has been shown to enhance the folding, trafficking and activity of a destabilized glucocerebrosidase (GC) variant in Gaucher Disease. In case of another LSD, Tay-Sachs disease, TFEB was shown to rescue the activity of a β-hexosaminidase mutant. The findings describe TFEB as specific regulator of lysosomal proteostasis and a therapeutic target to rescue enzyme homeostasis in LSDs (60,61).

Also it was reported that induction of lysosomal exocytosis by TFEB overexpression can rescue pathologic storage and restore normal cellular morphology LSDs (62). Apart from LSDs, TFEB has been shown to induce lipid catabolism and clearance and could rescue obesity and metabolic syndrome in mice (15, 16). Overall, in recent years TFEB has become a potentially important transcription factor for its role in not only lysosomal biogenesis but also due to its implications as a therapeutic target in disease conditions. Not many therapeutically viable compounds targeting TFEB activity have been identified although recently it was shown that 2-hydroxypropyl-β-cyclodextrin (HPβCD) is an FDA-approved excipient promotes TFEB-mediated clearance of proteolipid aggregates in cells from patients suffering from LINCL (56). Also another study revealed induction of TFEB levels and activity as well as lysosomal biogenesis by Genistein (5,7-dihydroxy-3-(4-hydroxyphenyl)-4H-1-benzopyran-4-one), a potential drug for the use in substrate reduction therapy (SRT) for mucopolysaccharidoses (MPSs) (63).

Recent studies have linked TFEB, lysosomal biogenesis and autophagy with lipid metabolism (14-16, 55, 64, 65). The potential interplay between TFEB and lipid metabolism led us to investigate the role of gemfibrozil and ATRA which are potential activators of PPARα and RXRα, two important factors in lipid metabolism. Gemfibrozil, marketed as 'Lopid', is FDA approved drugs prescribed for hyperlipidemia (17, 19), but it has been shown to have multiple beneficial effects (22). The ability of gemfibrozil to cross blood-brain-barrier (BBB) has already been documented (20). We have previously reported that gemfibrozil in conjunction with ATRA could induce the levels of Cln2 gene in brain cells (66). We further investigated to see whether TFEB, the master regulator of lysosomal biogenesis could be affected by the drugs. Our data indicates that gemfibrozil alone or in conjunction with ATRA could effectively induce the expression of TFEB in brain cells.

Further investigation suggested the possible role of PPARα in the process. PPARα has been shown to play significant role in different regulatory and modulatory pathways (67-71). Certain polyunsaturated fatty acids and oxidized derivatives and by lipid-modifying drugs of the fibrate family, including fenofibrate and gemfibrozil has been known to activate PPARα. Fibrate drugs replace the HSP90 repressor complex which sequesters PPARα in the cytosol and help to rescue the transcriptional activity of PPARα (21). Therefore, we assessed the role of the PPAR group of receptors for this phenomenon. Our data clearly indicate the involvement of PPARα, but not PPARβ and PPARγ, in the process of upregulation of TFEB by gemfibrozil. The in vitro studies were further validated by in vivo studies, in which we used the knockout mice for PPARα and PPARβ. Our in vivo results also supported the cell culture data.

An analysis of the promoter region of the Tfeb gene was performed to delineate the mechanism of upregulation of TFEB. A PERO site was found in the mouse Tfeb promoter as well as an RXR binding site. According to previous studies, PPAR/RXR heterodimer has shown DNA binding activity. (70). Together, the PPAR/RXR heterodimer regulates the transcription of genes for which products are involved in lipid homeostasis, cell growth, and differentiation (69, 72). The pathway of Tfeb upregulation was observed to require a co-operative effect of both PPAR and RXR. Furthermore, the effect of both gemfibrozil and RA were abrogated in the absence of either RXRα or PPARα. The luciferase assay results using both WT and mutant luciferase construct of the PERO on the Tfeb promoter showed increased Tfeb promoter dependant activity in the WT construct upon stimulation. But PPARα (−/−) cells when transfected with pTFEB(WT)-Luc construct and also WT cells when transfected with pTFEB(Mu)-Luc construct did not show any significant increase in the luciferase activity. Finally, the ChIP data indicated the recruitment of the PPARα and RXRα along with PGC1α and RNA Pol on the PERO site of the TFEB promoter. The experimental data was critically analyzed along with incorporation of proper controls to ensure the specificity of the findings.

Collectively, these data outline a unique mechanism where gemfibrozil, an activator of PPARα, and ATRA, an agonist of RXRα, together upregulate TFEB in brain cells via PPARα/RXRαheterodimer. Although one study reported that PPARγ-null trophoblast stem (TS) cells have lower levels of TFEB on Day 4 of differentiation, but a study using GW9662, a potent and known PPARγ antagonist in brain cells did not reveal any substantial involvement of PPARγ (73). This may be due to variation in cell types, i.e. differentiating TS cells vs matured primary brain astrocytes/neuron or differential level of potential for activation of PPARα. In one comprehensive study by Settembre et al., the authors reported that PPARα and PGC1α are targets of TFEB under starvation induced stress and that TFEB is autoregulated in case of starvation stress, but another study by Tsunemi et al. places PGC1α upstream to TFEB in Huntington's disease scenario. It is quite possible that TFEB regulates lipid metabolism via PPARα and PGC1α, both of which have very significant role in regulating lipid metabolism. But on the other hand the present data indicate that a direct stimulation of PPARα can induce the recruitment of PPARα-RXRα-PGC1α complex on TFEB promoter and thereby influencing lysosomal biogenesis.

While stress response directly regulates TFEB function, the present finding suggests that activation of PPARα as well as RXRα by external stimuli can also regulate TFEB, which may in turn control the expression of PPARα or other genes responsible for lipid metabolism. However, more detailed studies are necessary to decipher the presence of any such feed forward regulatory mechanism and the apparent bi-directional interplay between lipid metabolism and lysosomal biogenesis.

In summary, this study tests a novel hypothesis that lipid lowering drugs like gemfibrozil can upregulate lysosomal biogenesis in brain cells via PPARα mediated activation of TFEB. Considering the important roles played by TFEB in certain disease scenarios there is a growing interest in identifying TFEB as a therapeutic target. The outcome of this investigation highlights undiscovered properties of PPARα, describe a new treatment option for LSDs, and reveal a more dynamic regulation of TFEB and fuel interest in understanding the link between the lipid metabolism pathway and lysosomal biogenesis.

Figure 9:
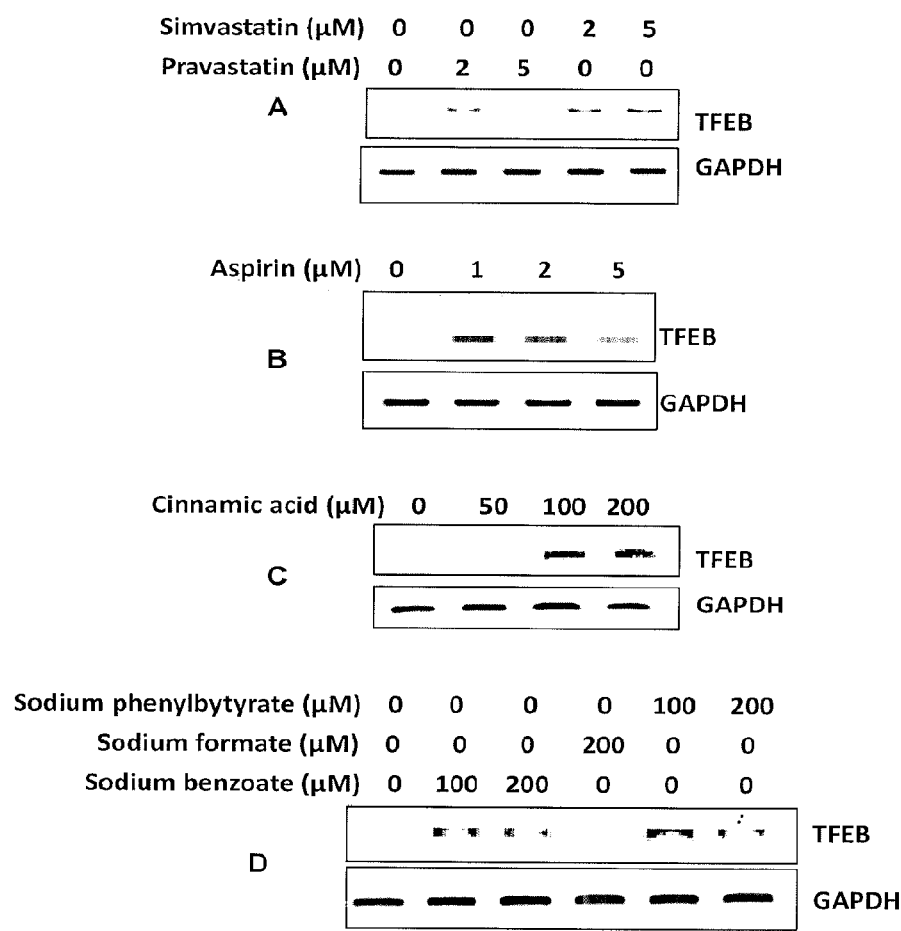
FIGS. 9(A)-9(D) illustrate the upregulation of TFEB mRNA expression in mouse astrocytes by cholesterol-lowering drugs (simvastatin and pravastatin), aspirin (anasgesic and anti-pyretic), cinnamic acid (metabolite of cinnamon), and drugs for urea cycle disorders (sodium phenylbutyrate and sodium benzoate).

Example 9—Upregulation of TFEB mRNA Expression in Mouse Astrocytes by Cholesterol-lowering Drugs FIG. 9 illustrates the upregulation of TFEB mRNA expression in mouse astrocytes by cholesterol-lowering drugs (simvastatin and pravastatin), aspirin (anasgesic and anti-pyretic), cinnamic acid (metabolite of cinnamon), and drugs for urea cycle disorders (sodium phenylbutyrate and sodium benzoate). Mouse primary astrocytes were incubated with different concentrations (see FIG. 9) of simvastatin and pravastatin (A), (B), cinnamic acid (C), and sodium phenyl-butyrate and sodium benzoate (D) for 5 hr. under serum-free condition followed by monitoring the mRNA expression of TFEB by semi-quantitative RT-PCR. Sodium formate (D) was used as a negative control for sodium phenylbutyrate and sodium benzoate.

Example 10—Aspirin Induces Lysosomal Biogenesis in Primary Mouse Astrocytes

Figure 10:
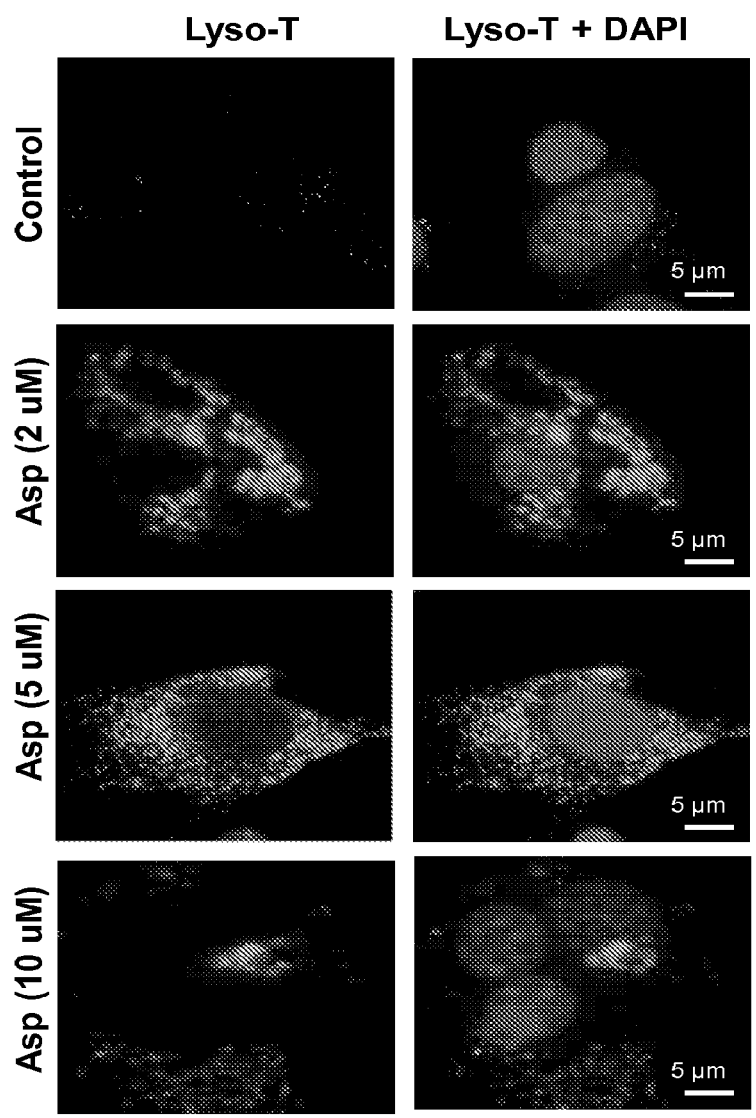
FIG. 10 illustrates an increase in lysosomal biogenesis by aspirin in primary mouse astrocytes. Cells were treated with different concentrations of aspirin for 24 h under serum-free condition followed by Lyso-tracker staining. Results represent three independent experiments.

We examined whether aspirin, one of the most widely used medications in the world, could upregulate lysosomal biogenesis in mouse brain cells. Astrocytes were treated in serum-free media with different doses of aspirin followed by lyso-tracker staining. Aspirin at doses of 2 and 5 µM markedly increased lysosomal biogenesis in astrocytes as evident from increased lyso-tracker staining (FIG. 10). However, at a dose of 10 µM, aspirin was not very potent in increasing lysosomal biogenesis (FIG. 10).

Example 11—Aspirin Increases the Expression of LAMP2 in Primary Mouse Astrocytes LAMP2 is an important lysosomal membrane protein, which plays a key role in the formation of new lysosomes.

We observed time-dependent increase in LAMP2 mRNA (FIG. 11A) and protein (FIG. 11C) expression by aspirin in astrocytes. Again dose-dependent experiment showed increase in LAMP2 protein expression at doses of 2 and 5 µM of aspirin (FIG. 11B). LAMP2 increase by aspirin was further confirmed by immunostaining (FIG. 11D).

Example 12—Aspirin Upregulates the Expression and Activity of TPP1 in Primary Mouse Astrocytes Tripeptidylpeptidase 1 (TPP1) is the target molecule in late infantile Batten disease as the activity of this protein is deficient in this disease. We examined if aspirin could upregulate TPP1 in astrocytes. Again, dose-dependent studies showed increase in TPP1 protein at lower doses (2 and 5 µM) of aspirin (FIG. 12A). Increase in TPP1 protein in response to 5 µM aspirin was evident as early as 2 h, which was maximum at 12 h of incubation (FIG. 12B). Again, we observed increase in TPP1 activity at 2 and 5 µM, but not 10 µM, aspirin (FIG. 12C).

Example 13—Aspirin Upregulates the Expression of TFEB in Primary Mouse Astrocytes According to recent findings, TFEB is a master regulator of lysosomal biogenesis (9, 12, 25). Over the years, different groups have underscored the role of lysosome in different disease scenarios (48, 49, 52, 53). Lysosome-related genes are reported to be closely regulated in the orbital fat of patients suffering from Graves' ophthalmopathy whereas down-regulation of lysosomal processing improved pegylated lipopolyplex-mediated gene transfection (53, 54). The increase in lysosomal biogenesis may not necessarily prove to be beneficial in all disease and cell types, but in some cases induction of the autophagy-lysosomal pathway could be helpful for cellular clearance of toxic wastes (55, 56). Over the past few years, TFEB has emerged as a potential therapeutic target for some lysosome-related diseases. According to Tsunemi et al (57), activation of transcription factor EB (TFEB) via PGC1α may result in increased htt turnover and the elimination of protein aggregates. There are reports suggesting a link between α-synuclein toxcitiy and impaired function of TFEB and identified TFEB as a target for neuroprotective therapy in PD (59). TFEB activation has also been shown to enhance the folding, trafficking and activity of a destabilized glucocerebrosidase (GC) variant in Gaucher Disease. In case of Tay-Sachs disease, another LSD, TFEB has been shown to rescue the activity of a β-hexosaminidase mutant. These findings describe TFEB as specific regulator of lysosomal proteostasis and a therapeutic target to rescue enzyme homeostasis in LSDs (60, 61).

Therefore, we examined if aspirin could upregulate TFEB in astrocytes. Dose-dependent studies showed that aspirin was able to increase the protein level of TFEB at doses of 2 and 5 µM aspirin (FIG. 13A). TFEB upregulation by aspirin was further confirmed by immunofluorescence analysis (FIG. 13B). We also cloned the Tfeb promoter into the pGL3 Enhancer vector and examined reporter activity driven by the Tfeb promoter. Interestingly, aspirin induced Tfeb promoter driven luciferase activity in astrocytes (FIG. 13C), suggesting that aspirin increases the transcription of the Tfeb gene.

Example 14—Aspirin Induces the Activation of PPARα in Primary Mouse Astrocytes

Recently we have discovered that PPARα plays a key role in the transcription of Tfeb. Therefore, here, we examined if aspirin could induce the activation of PPARα in astrocytes. First, we employed electrophoretic mobility shift assay (EMSA) to monitor the DNA-binding activity of PPARα and found time-dependent increase in PPARα activation by aspirin (FIG. 14A). To confirm these results, we isolated astrocytes from WT, PPARα (−/−) and PPARβ (−/−) mice and monitored the transcriptional activity of PPAR. Interestingly, aspirin increased PPRE-driven luciferase activity in astrocytes isolated from WT and PPARβ (−/−), but not PPARα (−/−), mice (FIG. 14B), suggesting that aspirin is capable of inducing the activation of PPARα, but not PPARβ.

Example 15—Aspirin Upregulates TFEB in Primary Mouse Astrocytes via PPARα

Astrocytes isolated from WT, PPARα (−/−) and PPARβ (−/−) mice were treated with 5 µM aspirin followed by immunofluorescence analysis of TFEB. FIG. 15 shows that aspirin induced the expression of TFEB in astrocytes isolated from WT and PPARβ (−/−), but not PPARα (−/−), mice. These results indicate that aspirin requires PPARα, but not PPARβ, for increasing TFEB in astrocytes.

Example 16—Aspirin Increases Lysosomal Biogenesis in Primary Mouse Astrocytes via PPARα

Because TFEB is the master regulator of lysosomal gene expression and biogenesis (9, 12, 16), we examined the effect of aspirin on lysosomal biogenesis. Astrocytes isolated from WT, PPARα (−/−) and PPARβ (−/−) mice were treated with different doses aspirin followed by monitoring the level of LAMP2. As evident from FIG. 16A-B, aspirin dose-dependently increased the level of LAMP2 in astrocytes isolated from WT and PPARβ (−/−), but not PPARα (−/−), mice. We also examined the status of lysosomes by lyso-tracker staining. Similar to LAMP2 results, aspirin increased lysosomal biogenesis in astrocytes isolated from WT and PPARβ (−/−), but not PPARα (−/−), mice (FIG. 17).

Example 17—Discussion of Examples 10 to 16

There are several advantages of aspirin over other available therapies for lysosomal storage disorders. In one hand, aspirin has been widely used as an analgesic throughout the world for decades. On the other, it can be taken orally, the least painful route. Although aspirin has been reported to exhibit some toxic effects (gastric ulcers, stomach bleeding, and tinnitus etc.) at high doses (74), in our study, aspirin is boosting lysosomal biogenesis at low doses (2 and 5 µM) and at low doses, aspirin may not be toxic. However, if aspirin exhibits any toxic effects even at lower doses (e.g. gastric ulcer), there are ways to reduce its side effects. For example, enteric-coated aspirin is available for oral use and to avoid the degradation in the stomach. In an open randomized trial, low dose of aspirin in slow-releasing formulation showed efficacy as an anti-platelet agent (75) without much noticeable side effect. One research study (76) used S-adenosyl-methionine (SAM), an amino acid naturally formed in the body and found that a dose of 500 mg SAM given together with a large dose of aspirin (1300 mg) reduced the amount of stomach damage by 90 percent.

In summary, we have demonstrated that aspirin, a widely-used analgesic, increases lysosomal biogenesis in astrocytes via PPARα-mediated upregulation of TFEB. These results highlight that this drug may be used for therapeutic intervention in late infantile Batten disease and other LSDs as primary or adjunct therapy.

REFERENCES 1. de Duve, C. (1959) Lysosomes, a new group of cytoplasmic particles. *Subcellular particles* 60, 128-159
2. De Duve, C., and Wattiaux, R. (1966) Functions of lysosomes. *Annu Rev Physiol* 28, 435-492
3. Saftig, P. (2006) Physiology of the lysosome.
4. Perez-Sala, D., Boya, P., Ramos, I., Herrera, M., and Stamatakis, K. (2009) The C-terminal sequence of RhoB directs protein degradation through an endolysosomal pathway. *PLoS One* 4, e8117
5. Fuster, J. J., Gonzalez, J. M., Edo, M. D., Viana, R., Boya, P., Cervera, J., Verges, M., Rivera, J., and Andres, V. (2010) Tumor suppressor p27(Kip1) undergoes endolysosomal degradation through its interaction with sorting nexin 6. *FASEB J* 24, 2998-3009
6. Korolchuk, V. I., Saiki, S., Lichtenberg, M., Siddiqi, F. H., Roberts, E. A., Imarisio, S., Jahreiss, L., Sarkar, S., Futter, M., Menzies, F. M., O'Kane, C. J., Deretic, V., and Rubinsztein, D. C. (2011) Lysosomal positioning coordinates cellular nutrient responses. *Nat Cell Biol* 13, 453-460
7. Boya, P., and Kroemer, G. (2008) Lysosomal membrane permeabilization in cell death. *Oncogene* 27, 6434-6451
8. Martina, J. A., Diab, H. I., Lishu, L., Jeong, A. L., Patange, S., Raben, N., and Puertollano, R. (2014) The nutrient-responsive transcription factor TFE3 promotes autophagy, lysosomal biogenesis, and clearance of cellular debris. *Sci Signal* 7, ra9
9. Palmieri, M., Impey, S., Kang, H., di Ronza, A., Pelz, C., Sardiello, M., and Ballabio, A. (2011) Characterization of the CLEAR network reveals an integrated control of cellular clearance pathways. *Hum Mol Genet* 20, 3852-3866
10. Sardiello, M., Palmieri, M., di Ronza, A., Medina, D. L., Valenza, M., Gennarino, V. A., Di Malta, C., Donaudy, F., Embrione, V., Polishchuk, R. S., Banfi, S., Parenti, G., Cattaneo, E., and Ballabio, A. (2009) A gene network regulating lysosomal biogenesis and function. *Science* 325, 473-477
11. Marschner, K., Kollmann, K., Schweizer, M., Braulke, T., and Pohl, S. (2011) A key enzyme in the biogenesis of lysosomes is a protease that regulates cholesterol metabolism. *Science* 333, 87-90
12. Settembre, C., Di Malta, C., Polito, V. A., Garcia Arencibia, M., Vetrini, F., Erdin, S., Erdin, S. U., Huynh, T., Medina, D., Colella, P., Sardiello, M., Rubinsztein, D. C., and Ballabio, A. (2011) TFEB links autophagy to lysosomal biogenesis. *Science* 332, 1429-1433
13. Ferron, M., Settembre, C., Shimazu, J., Lacombe, J., Kato, S., Rawlings, D. J., Ballabio, A., and Karsenty, G. (2013) A RANKL-PKCbeta-TFEB signaling cascade is necessary for lysosomal biogenesis in osteoclasts. *Genes Dev* 27, 955-969
14. Settembre, C., Zoncu, R., Medina, D. L., Vetrini, F., Erdin, S., Huynh, T., Ferron, M., Karsenty, G., Vellard, M. C., Facchinetti, V., Sabatini, D. M., and Ballabio, A. (2012) A lysosome-to-nucleus signalling mechanism senses and regulates the lysosome via mTOR and TFEB. *EMBO J* 31, 1095-1108
15. Settembre, C., Fraldi, A., Medina, D. L., and Ballabio, A. (2013) Signals from the lysosome: a control centre for cellular clearance and energy metabolism. *Nat Rev Mol Cell Biol* 14, 283-296
16. Settembre, C., De Cegli, R., Mansueto, G., Saha, P. K., Vetrini, F., Visvikis, O., Huynh, T., Carissimo, A., Palmer, D., Klisch, T. J., Wollenberg, A. C., Di Bernardo, D., Chan, L., Irazoqui, J. E., and Ballabio, A. (2013) TFEB controls cellular lipid metabolism through a starvation-induced autoregulatory loop. *Nat Cell Biol* 15, 647-658
17. Robins, S. J., Collins, D., Wittes, J. T., Papademetriou, V., Deedwania, P. C., Schaefer, E. J., McNamara, J. R., Kashyap, M. L., Hershman, J. M., Wexler, L. F., and Rubins, H. B. (2001) Relation of gemfibrozil treatment and lipid levels with major coronary events: VA-HIT: a randomized controlled trial. *JAMA* 285, 1585-1591
18. Rubins, H. B., and Robins, S. J. (1992) Effect of reduction of plasma triglycerides with gemfibrozil on high-density-lipoprotein-cholesterol concentrations. *J Intern Med* 231, 421-426
19. Rubins, H. B., Robins, S. J., Collins, D., Fye, C. L., Anderson, J. W., Elam, M. B., Faas, F. H., Linares, E., Schaefer, E. J., Schectman, G., Wilt, T. J., and Wittes, J. (1999) Gemfibrozil for the secondary prevention of coronary heart disease in men with low levels of high-density lipoprotein cholesterol. Veterans Affairs High-Density Lipoprotein Cholesterol Intervention Trial Study Group. *N Engl J Med* 341, 410-418
20. Dasgupta, S., Roy, A., Jana, M., Hartley, D. M., and Pahan, K. (2007) Gemfibrozil ameliorates relapsing-remitting experimental autoimmune encephalomyelitis independent of peroxisome proliferator-activated receptor-alpha. *Mol Pharmacol* 72, 934-946
21. Pahan, K., Jana, M., Liu, X., Taylor, B. S., Wood, C., and Fischer, S. M. (2002) Gemfibrozil, a lipidlowering drug, inhibits the induction of nitric-oxide synthase in human astrocytes. *J Biol Chem* 277, 45984-45991
22. Roy, A., and Pahan, K. (2009) Gemfibrozil, stretching arms beyond lipid lowering. *Immunopharmacol Immunotoxicol* 31, 339-351
23. Corbett, G. T., Roy, A., and Pahan, K. (2012) Gemfibrozil, a lipid-lowering drug, upregulates IL-1 receptor antagonist in mouse cortical neurons: implications for neuronal self-defense. *J Immunol* 189, 1002-1013
24. Brahmachari, S., and Pahan, K. (2007) Sodium benzoate, a food additive and a metabolite of cinnamon, modifies T cells at multiple steps and inhibits adoptive transfer of experimental allergic encephalomyelitis. *J Immunol* 179, 275-283
25. Saha, R. N., and Pahan, K. (2007) Differential regulation of Mn-superoxide dismutase in neurons and astroglia by HIV-1 gp120: Implications for HIV-associated dementia. *Free Radic Biol Med* 42, 1866-1878
26. Giulian, D., and Baker, T. J. (1986) Characterization of ameboid microglia isolated from developing mammalian brain. *J Neurosci* 6, 2163-2178
27. Jana, M., and Pahan, K. (2005) Redox regulation of cytokine-mediated inhibition of myelin gene expression in human primary oligodendrocytes. *Free Radic Biol Med* 39, 823-831
28. Khasnavis, S., Jana, A., Roy, A., Wood, T., Ghosh, S., Watson, R., and Pahan, K. Suppression of nuclear factor-kappa B activation and inflammation in microglia by a physically-modified saline. *J Biol Chem*
29. Khasnavis, S., and Pahan, K. Sodium benzoate, a metabolite of cinnamon and a food additive, upregulates neuroprotective Parkinson disease protein DJ-1 in astrocytes and neurons. J Neuroimmune Pharmacol 7, 424-435
30. Dasgupta, S., Jana, M., Zhou, Y., Fung, Y. K., Ghosh, S., and Pahan, K. (2004) Antineuroinflammatory effect of NF-kappaB essential modifier-binding domain peptides in the adoptive transfer model of experimental allergic encephalomyelitis. J Immunol 173, 1344-1354
31. Corbett, G. T., Roy, A., and Pahan, K. Gemfibrozil, a Lipid-Lowering Drug, Upregulates IL-1 Receptor Antagonist in Mouse Cortical Neurons: Implications for Neuronal Self-Defense. J Immunol 189, 1002-1013
32. Saha, R. N., Liu, X., and Pahan, K. (2006) Up-regulation of BDNF in astrocytes by TNF-alpha: a case for the neuroprotective role of cytokine. J Neuroimmune Pharmacol 1, 212-222
33. Jana, M., Jana, A., Liu, X., Ghosh, S., and Pahan, K. (2007) Involvement of phosphatidylinositol 3- kinase-mediated up-regulation of I kappa B alpha in anti-inflammatory effect of gemfibrozil in microglia. J Immunol 179, 4142-4152
34. Jana, M., and Pahan, K. Gemfibrozil, a lipid lowering drug, inhibits the activation of primary human microglia via peroxisome proliferator-activated receptor beta. Neurochem Res 37, 1718-1729
35. Nelson, J. D., Denisenko, O., and Bomsztyk, K. (2006) Protocol for the fast chromatin immunoprecipitation (ChIP) method. Nat Protoc 1, 179-185
36. Cullingford, T. E., Bhakoo, K., Peuchen, S., Dolphin, C. T., Patel, R., and Clark, J. B. (1998) Distribution of mRNAs encoding the peroxisome proliferator-activated receptor alpha, beta, and gamma and the retinoid X receptor alpha, beta, and gamma in rat central nervous system. J Neurochem 70, 1366-1375
37. Nishizawa, H., Manabe, N., Morita, M., Sugimoto, M., Imanishi, S., and Miyamoto, H. (2003) Effects of in utero exposure to bisphenol A on expression of RARalpha and RXRalpha mRNAs in murine embryos. J Reprod Dev 49, 539-545
38. Chinetti, G., Griglio, S., Antonucci, M., Torra, I. P., Delerive, P., Majd, Z., Fruchart, J. C., Chapman, J., Najib, J., and Staels, B. (1998) Activation of proliferator-activated receptors alpha and gamma induces apoptosis of human monocyte-derived macrophages. J Biol Chem 273, 25573-25580
39. Brun, S., Carmona, M. C., Mampel, T., Vinas, O., Giralt, M., Iglesias, R., and Villarroya, F. (1999) Activators of peroxisome proliferator-activated receptor-alpha induce the expression of the uncoupling protein-3 gene in skeletal muscle: a potential mechanism for the lipid intakedependent activation of uncoupling protein-3 gene expression at birth. Diabetes 48, 1217-1222
40. Chinetti, G., Lestavel, S., Bocher, V., Remaley, A. T., Neve, B., Torra, I. P., Teissier, E., Minnich, A., Jaye, M., Duverger, N., Brewer, H. B., Fruchart, J. C., Clayey, V., and Staels, B. (2001) PPAR-alpha and PPAR-gamma activators induce cholesterol removal from human macrophage foam cells through stimulation of the ABCA1 pathway. Nat Med 7, 53-58
41. Kelly, D. P. (2001) The pleiotropic nature of the vascular PPAR gene regulatory pathway. Circ Res 89, 935-937
42. Boitier, E., Gautier, J. C., and Roberts, R. (2003) Advances in understanding the regulation of apoptosis and mitosis by peroxisome-proliferator activated receptors in pre-clinical models: relevance for human health and disease. Comp Hepatol 2, 3
43. Pshezhetsky, A. V., and Ashmarina, M. (2001) Lysosomal multienzyme complex: biochemistry, genetics, and molecular pathophysiology. Prog Nucleic Acid Res Mol Biol 69, 81-114
44. Karageorgos, L. E., Isaac, E. L., Brooks, D. A., Ravenscroft, E. M., Davey, R., Hopwood, J. J., and Meikle, P. J. (1997) Lysosomal biogenesis in lysosomal storage disorders. Exp Cell Res 234, 85-97
45. Weissmann, G. (1967) The role of lysosomes in inflammation and disease. Annu Rev Med 18, 97-112
46. Eskelinen, E. L., Tanaka, Y., and Saftig, P. (2003) At the acidic edge: emerging functions for lysosomal membrane proteins. Trends Cell Biol 13, 137-145
47. Brignull, L. M., Czimmerer, Z., Saidi, H., Daniel, B., Villela, I., Bartlett, N. W., Johnston, S. L., Meira, L. B., Nagy, L., and Nohturfft, A. (2013) Reprogramming of lysosomal gene expression by interleukin-4 and Stat6. BMC Genomics 14, 853
48. Neufeld, E. F. (1991) Lysosomal storage diseases. Annu Rev Biochem 60, 257-280
49. Gieselmann, V. (1995) Lysosomal storage diseases. Biochim Biophys Acta 1270, 103-136
50. Khatiwada, B., and Pokharel, A. (2009) Lysosomal storage disease. JNMA J Nepal Med Assoc 48, 242-245
51. Jolly, R. D. (1978) LYSOSOMAL STORAGE DISEASES. Neuropathology and Applied Neurobiology 4, 419-427
52. Appelqvist, H., Waster, P., Kagedal, K., and Ollinger, K. (2013) The lysosome: from waste bag to potential therapeutic target. J Mol Cell Biol 5, 214-226
53. Bai, J., Liu, Y., Sun, W., Chen, J., Miller, A. D., and Xu, Y. (2013) Down-regulated lysosomal processing improved pegylated lipopolyplex-mediated gene transfection. J Gene Med 15, 182-192
54. Chen, M. H., Liao, S. L., Tsou, P. L., Shih, M. J., Chang, T. C., and Chuang, L. M. (2008) Lysosomerelated genes are regulated in the orbital fat of patients with graves' ophthalmopathy. Invest Ophthalmol Vis Sci 49, 4760-4764
55. Sarkar, S., Carroll, B., Buganim, Y., Maetzel, D., Ng, A. H., Cassady, J. P., Cohen, M. A., Chakraborty, S., Wang, H., Spooner, E., Ploegh, H., Gsponer, J., Korolchuk, V. I., and Jaenisch, R. (2013) Impaired autophagy in the lipid-storage disorder Niemann-Pick type C1 disease. Cell Rep 5, 1302-1315
56. Song, W., Wang, F., Lotfi, P., Sardiello, M., and Segatori, L. (2014) 2-Hydroxypropyl-betacyclodextrin promotes transcription factor EB-mediated activation of autophagy: implications for therapy. J Biol Chem 289, 10211-10222
57. Tsunemi, T., Ashe, T. D., Morrison, B. E., Soriano, K. R., Au, J., Roque, R. A., Lazarowski, E. R., Damian, V. A., Masliah, E., and La Spada, A. R. (2012) PGC-1alpha rescues Huntington's disease proteotoxicity by preventing oxidative stress and promoting TFEB function. Sci Transl Med 4, 142ra197
58. La Spada, A. R. (2012) PPARGC1A/PGC-1alpha, TFEB and enhanced proteostasis in Huntington disease: defining regulatory linkages between energy production and protein-organelle quality control. Autophagy 8, 1845-1847
59. Decressac, M., Mattsson, B., Weikop, P., Lundblad, M., Jakobsson, J., and Bjorklund, A. (2013) TFEB-mediated autophagy rescues midbrain dopamine neurons from alpha-synuclein toxicity. Proc Natl Acad Sci USA 110, E1817-1826

60. Wang, F., and Segatori, L. (2013) Remodeling the proteostasis network to rescue glucocerebrosidase variants by inhibiting ER-associated degradation and enhancing ER folding. PLoS One 8, e61418
61. Song, W., Wang, F., Savini, M., Ake, A., di Ronza, A., Sardiello, M., and Segatori, L. (2013) TFEB regulates lysosomal proteostasis. Hum Mol Genet 22, 1994-2009
62. Medina, D. L., Fraldi, A., Bouche, V., Annunziata, F., Mansueto, G., Spampanato, C., Puri, C., Pignata, A., Martina, J. A., Sardiello, M., Palmieri, M., Polishchuk, R., Puertollano, R., and Ballabio, A. (2011) Transcriptional activation of lysosomal exocytosis promotes cellular clearance. Dev Cell 21, 421-430
63. Moskot, M., Montefusco, S., Jakobkiewicz-Banecka, J., Mozolewski, P., Wegrzyn, A., Di Bernardo, D., Wegrzyn, G., Medina, D. L., Ballabio, A., and Gabig-Ciminska, M. (2014) The phytoestrogen genistein modulates lysosomal metabolism and Transcription Factor EB (TFEB) activation. J Biol Chem
64. Xu, X., Grijalva, A., Skowronski, A., van Eijk, M., Serlie, M. J., and Ferrante, A. W., Jr. (2013) Obesity activates a program of lysosomal-dependent lipid metabolism in adipose tissue macrophages independently of classic activation. Cell Metab 18, 816-830
65. Singh, R., and Cuervo, A. M. (2012) Lipophagy: connecting autophagy and lipid metabolism. Int J Cell Biol 2012, 282041
66. Ghosh, A., Corbett, G. T., Gonzalez, F. J., and Pahan, K. (2012) Gemfibrozil and fenofibrate, Food and Drug Administration-approved lipid-lowering drugs, up-regulate tripeptidyl-peptidase 1 in brain cells via peroxisome proliferator-activated receptor alpha: implications for late infantile Batten disease therapy. J Biol Chem 287, 38922-38935
67. Xu, J., Racke, M. K., and Drew, P. D. (2007) Peroxisome proliferator-activated receptor-alpha agonist fenofibrate regulates IL-12 family cytokine expression in the CNS: relevance to multiple sclerosis. J Neurochem 103, 1801-1810
68. Xu, J., Chavis, J. A., Racke, M. K., and Drew, P. D. (2006) Peroxisome proliferator-activated receptor-alpha and retinoid X receptor agonists inhibit inflammatory responses of astrocytes. J Neuroimmunol 176, 95-105
69. Krey, G., Mahfoudi, A., and Wahli, W. (1995) Functional interactions of peroxisome proliferatoractivated receptor, retinoid-X receptor, and Sp1 in the transcriptional regulation of the acylcoenzyme- A oxidase promoter. Mol Endocrinol 9, 219-231
70. Juge-Aubry, C. E., Gorla-Bajszczak, A., Pernin, A., Lemberger, T., Wahli, W., Burger, A. G., and Meier, C. A. (1995) Peroxisome proliferator-activated receptor mediates cross-talk with thyroid hormone receptor by competition for retinoid X receptor. Possible role of a leucine zipper-like heptad repeat. J Biol Chem 270, 18117-18122
71. Roy, A., Jana, M., Corbett, G. T., Ramaswamy, S., Kordower, J. H., Gonzalez, F. J., and Pahan, K. (2013) Regulation of cyclic AMP response element binding and hippocampal plasticity-related genes by peroxisome proliferator-activated receptor alpha. Cell Rep 4, 724-737
72. Marcus, S. L., Miyata, K. S., Rachubinski, R. A., and Capone, J. P. (1995) Transactivation by PPAR/RXR heterodimers in yeast is potentiated by exogenous fatty acid via a pathway requiring intact peroxisomes. Gene Expr 4, 227-239
73. Parast, M. M., Yu, H., Ciric, A., Salata, M. W., Davis, V., and Milstone, D. S. (2009) PPARgamma regulates trophoblast proliferation and promotes labyrinthine tri-lineage differentiation. PLoS One 4, e8055
74. Leung, F. W. (2008) Risk factors for gastrointestinal complications in aspirin users: review of clinical and experimental data. Dig Dis Sci 53, 2604-2615
75. Budd, J. S., Allen, K., Walsh, A., and Bell, P. R. (1993) The effectiveness of low dose slow release aspirin as an antiplatelet agent. J R Soc Med 86, 261-263
76. Laudanno, O. M. (1987) Cytoprotective effect of S-adenosylmethionine compared with that of misoprostol against ethanol-, aspirin-, and stress-induced gastric damage. Am J Med 83, 43-47

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A method for treatment of a lysosomal storage disorder, comprising administering to a subject in need of such treatment a therapeutically effective amount of a composition comprising an agent that mediates upregulation of Transcription Factor EB, wherein Transcription Factor EB is upregulated by increasing Transcription Factor EB mRNA levels increasing Transcription Factor EB protein levels or activating a PPARα-RXRα heterodimer;
   wherein the agent is cinnamic acid; and
   wherein the lysosomal storage disorder is selected from the group consisting of Fabry disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, and Galactosialidosis.

2. The method of claim 1, wherein the composition further comprises a therapeutically effective amount of all-trans retinoic acid or vitamin A.

3. The method of claim 1, wherein the lysosomal storage disorder is a disorder of the autophagy pathway and wherein the agent increases lysosomal biogenesis.

4. The method of claim 1, wherein the lysosomal storage disorder is Tay-Sach' s disease.

5. A method for treatment of a lysosomal storage disorder, comprising administering to a subject in need of such treatment a composition comprising a therapeutically effective amount of an agent, wherein the agent comprises a combination of cinnamic acid and all-trans retionic acid, wherein the agent restores Transcription Factor EB activity;
   wherein Transcription Factor EB is restored by increasing Transcription Factor EB mRNA levels increasing Transcription Factor EB protein levels or activating a PPARα-RXRα heterodimer;
   wherein the lysosomal storage disorder is selected from the group consisting of Fabry disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, and Galactosialidosis.

6. The method of claim 5, wherein the composition further comprises a pharmaceutically acceptable carrier.

7. The composition of claim 1, wherein the therapeutically effective amount is an amount that results in a serum concentration of the agent to be at least about 50 μM for at least 5 hours.

8. The composition of claim 5, wherein the therapeutically effective amount is an amount that results in a serum concentration of the agent to be at least about 50 μM for at least 5 hours.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: artificial Mouse Tfeb primer, sense strand

<400> SEQUENCE: 1
aacaaaggca ccatcctcaa                                              20

<210> SEQ ID NO 2
<211> LENGTH: 20
<212> TYPE: DNA
<213> ORGANISM: Artificial Sequence
<220> FEATURE:
<223> OTHER INFORMATION: artificial Mouse Tfeb primer, antisense strand

<400> SEQUENCE: 2
cagctcggcc atattcacac                                              20

<210> SEQ ID NO 3
<211> LENGTH: 24
<212> TYPE: DNA
<213> ORGANISM: Artificial Sequence
<220> FEATURE:
<223> OTHER INFORMATION: artificial Mouse Lamp2 primer, sense strand

<400> SEQUENCE: 3
ggtgctggtc tttcaggctt gatt                                         24

<210> SEQ ID NO 4
<211> LENGTH: 24
<212> TYPE: DNA
<213> ORGANISM: Artificial Sequence
<220> FEATURE:
<223> OTHER INFORMATION: artificial Mouse Lamp2 primer, antisense strand

<400> SEQUENCE: 4
accacccaat ctaagagcag gact                                         24

<210> SEQ ID NO 5
<211> LENGTH: 20
<212> TYPE: DNA
<213> ORGANISM: Artificial Sequence
<220> FEATURE:
<223> OTHER INFORMATION: artificial Mouse Limp2 primer, sense strand

<400> SEQUENCE: 5
tgttgaaacg ggagacatca                                              20

<210> SEQ ID NO 6
<211> LENGTH: 20
<212> TYPE: DNA
<213> ORGANISM: Artificial Sequence
<220> FEATURE:
<223> OTHER INFORMATION: artificial Mouse Limp2 primer, antisense strand

<400> SEQUENCE: 6
tggtgacaac caaagtcgtg                                              20

<210> SEQ ID NO 7
<211> LENGTH: 20
<212> TYPE: DNA
<213> ORGANISM: Artificial Sequence
<220> FEATURE:
<223> OTHER INFORMATION: artificial Mouse Npc1 primer, sense strand

<400> SEQUENCE: 7
gggatgcccg tgcctgcaat                                              20

<210> SEQ ID NO 8
<211> LENGTH: 20
<212> TYPE: DNA
<213> ORGANISM: Artificial Sequence
<220> FEATURE:
<223> OTHER INFORMATION: artificial Mouse Npc1 primer, antisense strand

<400> SEQUENCE: 8
ctggcagcta catggccccg                                              20

<210> SEQ ID NO 9

-continued

```
<211> LENGTH: 20
<212> TYPE: DNA
<213> ORGANISM: Artificial Sequence
<220> FEATURE:
<223> OTHER INFORMATION: artificial Mouse Gapdh primer, sense strand

<400> SEQUENCE: 9
gcacagtcaa ggccgagaat                                               20

<210> SEQ ID NO 10
<211> LENGTH: 20
<212> TYPE: DNA
<213> ORGANISM: Artificial Sequence
<220> FEATURE:
<223> OTHER INFORMATION: artificial Mouse Gapdh primer, antisense strand

<400> SEQUENCE: 10
gccttctcca tggtggtgaa                                               20

<210> SEQ ID NO 11
<211> LENGTH: 33
<212> TYPE: DNA
<213> ORGANISM: Artificial Sequence
<220> FEATURE:
<223> OTHER INFORMATION: artificial Tfeb primer, sense strand

<400> SEQUENCE: 11
acgcgtccag gagccaggga cggggtacat ctc                                33

<210> SEQ ID NO 12
<211> LENGTH: 33
<212> TYPE: DNA
<213> ORGANISM: Artificial Sequence
<220> FEATURE:
<223> OTHER INFORMATION: artificial Tfeb primer, antisense strand

<400> SEQUENCE: 12
agatctaagg agaaactgag tccgggcaga agg                                33

<210> SEQ ID NO 13
<211> LENGTH: 39
<212> TYPE: DNA
<213> ORGANISM: Artificial Sequence
<220> FEATURE:
<223> OTHER INFORMATION: artificial primer for mutated promoter site,
      sense strand

<400> SEQUENCE: 13
gcaacagcaa gtgcggattt gagggggggg gacggtggg                          39

<210> SEQ ID NO 14
<211> LENGTH: 39
<212> TYPE: DNA
<213> ORGANISM: Artificial Sequence
<220> FEATURE:
<223> OTHER INFORMATION: artificial primer for mutated promoter site,
      antisense strand

<400> SEQUENCE: 14
cccaccgtcc cccccctca aatccgcact tgctgttgc                           39

<210> SEQ ID NO 15
<211> LENGTH: 20
<212> TYPE: DNA
<213> ORGANISM: Artificial Sequence
<220> FEATURE:
<223> OTHER INFORMATION: artificial Set1 primer, sense strand
```

```
<400> SEQUENCE: 15
gaacattcca ggtggaggca                                               20

<210> SEQ ID NO 16
<211> LENGTH: 20
<212> TYPE: DNA
<213> ORGANISM: Artificial Sequence
<220> FEATURE:
<223> OTHER INFORMATION: artificial Set1 primer, antisense strand

<400> SEQUENCE: 16
cccccaacac atgcttctct                                               20

<210> SEQ ID NO 17
<211> LENGTH: 20
<212> TYPE: DNA
<213> ORGANISM: Artificial Sequence
<220> FEATURE:
<223> OTHER INFORMATION: artificial Set2 primer, sense strand

<400> SEQUENCE: 17
gagtctctcg gaggaggtga                                               20

<210> SEQ ID NO 18
<211> LENGTH: 20
<212> TYPE: DNA
<213> ORGANISM: Artificial Sequence
<220> FEATURE:
<223> OTHER INFORMATION: artificial Set2 primer, antisense strand

<400> SEQUENCE: 18
actccaggca tgctttctcc                                               20
```